(12) United States Patent
Yoshioka et al.

(10) Patent No.: US 11,569,450 B2
(45) Date of Patent: Jan. 31, 2023

(54) PHOTOELECTRIC CONVERSIO ELEMENT, OPTICAL SENSOR, IMAGING ELEMENT, AND COMPOUND

(71) Applicant: FUJIFILM Corporation, Tokyo (JP)

(72) Inventors: Tomoaki Yoshioka, Kanagawa (JP); Eiji Fukuzaki, Kanagawa (JP); Tomoyuki Mashiko, Kanagawa (JP)

(73) Assignee: FUJIFILM Corporation, Tokyo (JP)

( * ) Notice: Subject to any disclaimer, the term of this patent is extended or adjusted under 35 U.S.C. 154(b) by 286 days.

(21) Appl. No.: 16/869,564

(22) Filed: May 7, 2020

(65) Prior Publication Data

US 2020/0266359 A1 Aug. 20, 2020

Related U.S. Application Data

(63) Continuation of application No. PCT/JP2018/041887, filed on Nov. 13, 2018.

(30) Foreign Application Priority Data

Nov. 17, 2017 (JP) .............................. JP2017-221982

(51) Int. Cl.
*H01L 51/00* (2006.01)
*C07D 495/14* (2006.01)
(Continued)

(52) U.S. Cl.
CPC ........ *H01L 51/0071* (2013.01); *C07D 495/04* (2013.01); *C07D 495/14* (2013.01);
(Continued)

(58) Field of Classification Search
None
See application file for complete search history.

(56) References Cited

U.S. PATENT DOCUMENTS

| 2013/0042918 A1 | 2/2013 | Evans et al. |
| 2013/0181202 A1 | 7/2013 | Yofu et al. |
| 2016/0149132 A1 | 5/2016 | Lim et al. |

FOREIGN PATENT DOCUMENTS

| JP | 2012077064 | 4/2012 |
| JP | 2014082483 | 5/2014 |
| JP | 2016102117 | 6/2016 |

OTHER PUBLICATIONS

"International Search Report (Form PCT/ISA/210) of PCT/JP2018/041887," dated Feb. 19, 2019, with English translation thereof, pp. 1-5.

(Continued)

*Primary Examiner* — Jay Yang
(74) *Attorney, Agent, or Firm* — JCIPRNET

(57) ABSTRACT

The present invention provides a photoelectric conversion element having excellent heat resistance. In addition, the present invention provides an optical sensor and an imaging element including the photoelectric conversion element. In addition, the present invention provides a compound applied to the photoelectric conversion element. The photoelectric conversion element according to the embodiment of the present invention including a conductive film, a photoelectric conversion film, and a transparent conductive film, in this order, in which the photoelectric conversion film contains a compound represented by Formula (1) or (2).

(1)

(Continued)

-continued (2)

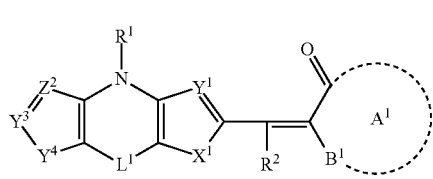

20 Claims, 4 Drawing Sheets

(51) Int. Cl.
*C07D 495/04* (2006.01)
*H01L 27/30* (2006.01)
*H01L 51/42* (2006.01)
*H01L 51/44* (2006.01)

(52) U.S. Cl.
CPC ...... *H01L 51/0053* (2013.01); *H01L 51/0058* (2013.01); *H01L 27/307* (2013.01); *H01L 51/4253* (2013.01); *H01L 51/442* (2013.01)

(56) References Cited

OTHER PUBLICATIONS

"International Preliminary Report On Patentability (Form PCT/IPEA/409) of PCT/JP2018/041887," completed on Aug. 22, 2019, with English translation thereof, pp. 1-9.

Agnieszka Nowak-Król, et al., "Modulation of band gap and p- versus n-semiconductor character of ADA dyes by core and acceptor group variation," Organic chemistry frontiers, vol. 3, Feb. 2016, pp. 545-555.

"Office Action of Taiwan Counterpart Application", dated Oct. 31, 2022, with partial English translation thereof, p. 1-p. 11.

PHOTOELECTRIC CONVERSIO ELEMENT, OPTICAL SENSOR, IMAGING ELEMENT, AND COMPOUND

CROSS-REFERENCE TO RELATED APPLICATIONS

This application is a Continuation of PCT International Application No. PCT/JP2018/041887 filed on Nov. 13, 2018, which claims priority under 35 U.S.C. § 119(a) to Japanese Patent Application No. 2017-221982 filed on Nov. 17, 2017. The above application is hereby expressly incorporated by reference, in its entirety, into the present application.

BACKGROUND OF THE INVENTION

1. Field of the Invention

The present invention relates to a photoelectric conversion element, an optical sensor, an imaging element, and a compound.

2. Description of the Related Art

In the related art, a planar solid-state imaging element in which photodiodes (PDs) are two-dimensionally arranged and a signal charge generated in each PD is read out by a circuit is widely used as a solid-state imaging element.

In order to realize a color solid-state imaging element, a structure in which a color filter transmitting light of a specific wavelength is disposed on a light incident surface side of the planar solid-state imaging element is generally used. Currently, a single plate solid-state imaging element in which the color filter transmitting blue (B) light, green (G) light, and red (R) light is regularly disposed on each PD which is two-dimensionally arranged is well known. However, in this single plate solid-state imaging element, light which is not transmitted through the color filter is not used, thus light utilization efficiency is poor.

In order to solve these disadvantages, in recent years, development of a photoelectric conversion element having a structure in which an organic photoelectric conversion film is disposed on a substrate for reading out a signal has progressed.

For example, JP2012-077064A discloses a compound represented by the following formula as a material applied to the photoelectric conversion element (claim 1).

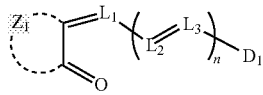

SUMMARY OF THE INVENTION

In recent years, further improvements are also required for various characteristics required for a photoelectric conversion element used in an imaging element and an optical sensor, along with demands for improving performance of the imaging element, the optical sensor, and the like.

For example, the photoelectric conversion element is required to have excellent heat resistance.

The present inventors have produced a photoelectric conversion element using the compound specifically disclosed in JP2012-077064A, and have evaluated heat resistance of the obtained photoelectric conversion element. As a result, the present inventors have found that the characteristics do not necessarily reach the level required recently and further improvement is necessary.

In view of the above-described circumstances, an object of the present invention is to provide a photoelectric conversion element having excellent heat resistance.

Another object of the invention is to provide an optical sensor and an imaging element including the photoelectric conversion element. Still another object of the invention is to provide a compound applied to the photoelectric conversion element.

The inventors of the invention have conducted extensive studies on the above-described problems. As a result, the inventors have found that it is possible to solve the above-described problems by applying the compound having a predetermined structure to the photoelectric conversion film, and have completed the invention.

[1] A photoelectric conversion element comprising:
a conductive film;
a photoelectric conversion film; and
a transparent conductive film in this order,
in which the photoelectric conversion film includes at least one compound selected from the group consisting of a compound represented by Formula (1) described later and a compound represented by Formula (2) described later.

[2] The photoelectric conversion element according to [1],
in which the compound represented by Formula (1) described later is a compound represented by Formula (3) described later, and
the compound represented by Formula (2) described later is a compound represented by Formula (4) described later.

[3] The photoelectric conversion element according to [1] or [2],
in which, in Formulae (1) to (4) described later, $L^1$ represents a single bond or $-CR^{a8}R^{a9}-$.

[4] The photoelectric conversion element according to any one of [1] to [3],
in which, in Formulae (1) to (4) described later, $X^1$ represents a sulfur atom, an oxygen atom, or a selenium atom.

[5] The photoelectric conversion element according to any one of [1] to [4],
in which the photoelectric conversion film includes a compound represented by Formula (5) described later.

[6] The photoelectric conversion element according to [5],
in which the compound represented by Formula (5) described later is a compound represented by Formula (6) described later.

[7] The photoelectric conversion element according to any one of claims [1] to [6],
in which, in Formulae (1) to (6) described later, $R^1$ represents an alkyl group which may have a substituent, an aryl group which may have a substituent, or a heteroaryl group which may have a substituent.

[8] The photoelectric conversion element according to any one of [1] to [7],
in which molecular weights of the compound represented by Formula (1) described later and the compound represented by Formula (2) described later are 400 to 900.

[9] The photoelectric conversion element according to any one of [1] to [8],
in which the photoelectric conversion film further includes an n-type organic semiconductor, and the photoelectric conversion film has a bulk hetero structure formed in a state in which the n-type organic semiconductor is mixed with the at least one compound selected from the group consisting of the compound represented by Formula (1) described later and the compound represented by Formula (2) described later.

[10] The photoelectric conversion element according to any one of [1] to [9], further comprising:
one or more interlayers between the conductive film and the transparent conductive film, in addition to the photoelectric conversion film.

[11] An optical sensor comprising the photoelectric conversion element according to any one of [1] to [10].

[12] An imaging element comprising the photoelectric conversion element according to any one of [1] to [10].

[13] A compound represented by Formula (5) described later.

According to the present invention, it is possible to provide a photoelectric conversion element having excellent heat resistance.

According to the invention, it is possible to provide an optical sensor and an imaging element including the photoelectric conversion element. According to the invention, it is possible to provide a compound applied to the photoelectric conversion element.

DESCRIPTION OF THE PREFERRED EMBODIMENTS

Figure 1A:
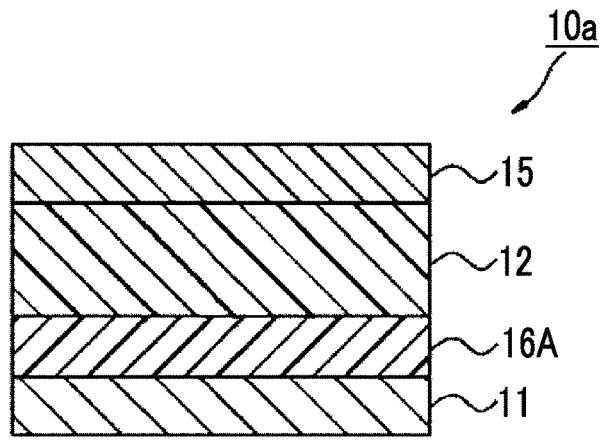
FIG. 1A is a schematic cross-sectional view showing an example of a configuration of a photoelectric conversion element.

Hereinafter, suitable embodiments of a photoelectric conversion element of the present invention will be described.

In the present specification, regarding a substituent or the like in which whether it is substituted or unsubstituted is not specified, within the scope not impairing an intended effect, the substituent or the like may be further substituted with a substituent (for example, a substituent W described later) or may not be substituted. For example, the expression of "alkyl group" refers to an alkyl group (that is, a substituted or unsubstituted alkyl group) which may be substituted with a substituent (for example, a substituent W described later).

In addition, in the present specification, the numerical range represented by using "to" means a range including numerical values denoted before and after "to" as a lower limit value and an upper limit value.

In the present specification, in a case of a plurality of substituents, linking groups, and the like (hereinafter, referred to as a substituent and the like) represented by specific reference numeral, or in a case of simultaneously defining a plurality of the substituent and the like, it means that each of the substituent and the like may be the same as or different with each other. The same applies to the definition of the number of the substituent and the like.

Photoelectric Conversion Element

A feature of the present invention compared to the related art is that at least one compound selected from the group consisting of a compound represented by Formula (1) described later and a compound represented by Formula (2) described later (hereinafter, these compounds are collectively referred to as a "specific compound") is used for a photoelectric conversion film.

The present inventors consider that, since the specific compound has a rigid structure, heat resistance of the photoelectric conversion element produced using the specific compound is improved.

Figure 1B:
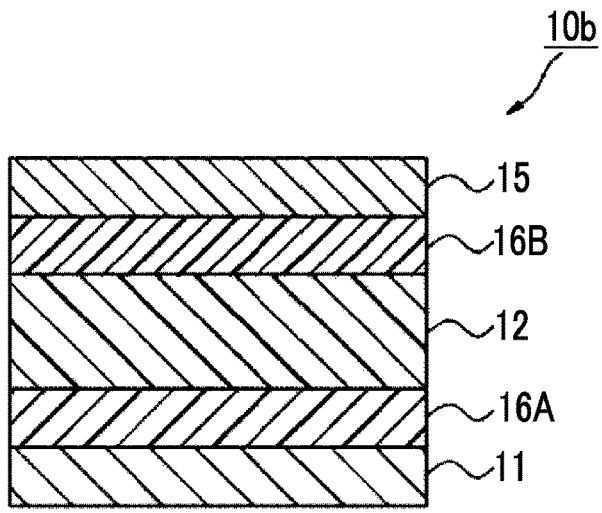
FIG. 1B is a schematic cross-sectional view showing an example of a configuration of a photoelectric conversion element.

Hereinafter, suitable embodiments of the photoelectric conversion element of the present invention will be described with reference to the drawings. FIGS. 1A and 1B show schematic cross-sectional views of one embodiment of the photoelectric conversion element of the present invention.

A photoelectric conversion element 10a shown in FIG. 1A has a configuration in which a conductive film (hereinafter, also referred to as a lower electrode) 11 functioning as the lower electrode, an electron blocking film 16A, a photoelectric conversion film 12 including the specific compound described later, and a transparent conductive film (hereinafter, also referred to as an upper electrode) 15 functioning as the upper electrode are laminated in this order.

FIG. 1B shows an example of a configuration of another photoelectric conversion element. A photoelectric conversion element 10b shown in FIG. 1B has a configuration in which the electron blocking film 16A, the photoelectric conversion film 12, a positive hole blocking film 16B, and the upper electrode 15 are laminated on the lower electrode 11 in this order. The lamination order of the electron blocking film 16A, the photoelectric conversion film 12, and the positive hole blocking film 16B in FIGS. 1A and 1B may be appropriately changed depending on use and characteristics.

In the photoelectric conversion element 10a (or 10b), it is preferable that light is incident on the photoelectric conversion film 12 through the upper electrode 15.

In a case where the photoelectric conversion element 10a (or 10b) is used, the voltage can be applied. In this case, it is preferable that the lower electrode 11 and the upper electrode 15 form a pair of electrodes and the voltage of $1 \times 10^{-5}$ to $1 \times 10^7$ V/cm is applied thereto. From the viewpoint of performance and power consumption, the voltage to be applied is more preferably $1 \times 10^{-4}$ to $1 \times 10^7$ V/cm and still more preferably $1 \times 10^{-3}$ to $5 \times 10^6$ V/cm.

The voltage application method is preferable that the voltage is applied such that the electron blocking film 16A side is a cathode and the photoelectric conversion film 12 side is an anode, in FIGS. 1A and 1B. In a case where the photoelectric conversion element 10a (or 10b) is used as an optical sensor, or also in a case where the photoelectric conversion element 10a (or 10b) is incorporated in an imaging element, the voltage can be applied by the same method.

As described in detail below, the photoelectric conversion element 10a (or 10b) can be suitably applied to use of the optical sensor and the imaging element.

Figure 2:
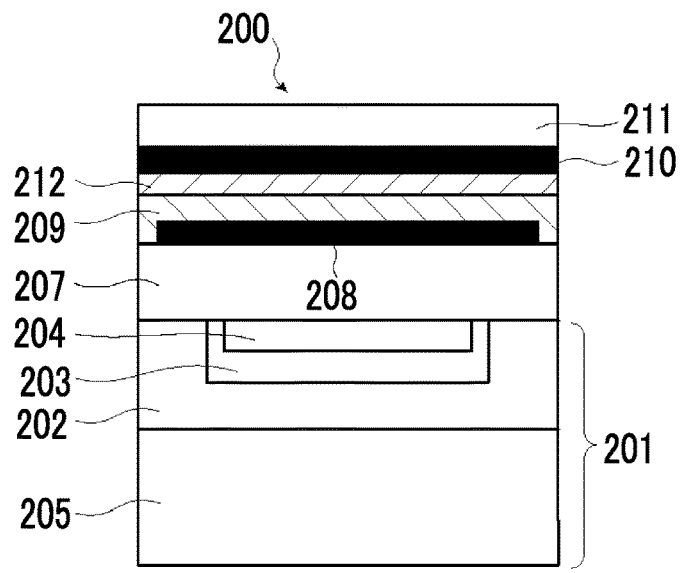
FIG. 2 is a schematic cross-sectional view of one pixel of a hybrid type photoelectric conversion element.

In addition, a schematic cross-sectional view of another embodiment of the photoelectric conversion element of the present invention is shown in FIG. 2.

The photoelectric conversion element 200 shown in FIG. 2 is a hybrid type photoelectric conversion element comprising an organic photoelectric conversion film 209 and an inorganic photoelectric conversion film 201. The organic photoelectric conversion film 209 includes the specific compound described later.

The inorganic photoelectric conversion film 201 has an n-type well 202, a p-type well 203, and an n-type well 204 on a p-type silicon substrate 205.

Blue light is photoelectrically converted at a p-n junction formed between the p-type well 203 and the n-type well 204 (a B pixel), and red light is photoelectrically converted at a p-n junction formed between the p-type well 203 and the n-type well 202 (an R pixel). The conduction types of the n-type well 202, the p-type well 203, and the n-type well 204 are not limited thereto.

Furthermore, a transparent insulating layer 207 is disposed on the inorganic photoelectric conversion film 201.

A transparent pixel electrode 208 divided for each pixel is disposed on the insulating layer 207. The organic photoelectric conversion film 209 which absorbs green light and performs photoelectric conversion is disposed on the transparent pixel electrode 208 in a single sheet configuration commonly for each pixel. The electron blocking film 212 is disposed on the organic photoelectric conversion film 209 in a single sheet configuration commonly for each pixel. A transparent common electrode 210 with a single sheet configuration is disposed on the electron blocking film 212. A transparent protective film 211 is disposed on the uppermost layer. The lamination order of the electron blocking film 212 and the organic photoelectric conversion film 209 may be reversed from that in FIG. 2, and the common electrode 210 may be disposed so as to be divided for each pixel.

The organic photoelectric conversion film 209 constitutes a G pixel for detecting green light.

The pixel electrode 208 is the same as the lower electrode 11 of the photoelectric conversion element 10a shown in FIG. 1A. The common electrode 210 is the same as the upper electrode 15 of the photoelectric conversion element 10a shown in FIG. 1A.

In a case where light from a subject is incident on the photoelectric conversion element 200, green light in the incident light is absorbed by the organic photoelectric conversion film 209 to generate electric charge of light. From the pixel electrode 208, the electric charge of light flows into and is accumulated in a green signal charge accumulation region not shown in the drawing.

Mixed light of the blue light and the red light transmitted through the organic photoelectric conversion film 209 enters the inorganic photoelectric conversion film 201. The blue light having a short wavelength is photoelectrically converted mainly at a shallow portion (in the vicinity of the p-n junction formed between the p-type well 203 and the n-type well 204) of a semiconductor substrate (inorganic photoelectric conversion film) 201 to generate electric charge of light, and a signal is output to the outside. The red light having a long wavelength is photoelectrically converted mainly at a deep portion (in the vicinity of the p-n junction formed between the p-type well 203 and the n-type well 202) of the semiconductor substrate (inorganic photoelectric conversion film) 201 to generate electric charge of light, and a signal is output to the outside.

In a case where the photoelectric conversion element 200 is used in the imaging element, a signal readout circuit (an electric charge transfer path in a case of a charge coupled device (CCD) type, or a metal-oxide-semiconductor (MOS) transistor circuit in a case of a complementary metal oxide semiconductor (CMOS) type), or the green signal charge accumulation region is formed in a surface portion of the p-type silicon substrate 205. In addition, the pixel electrode 208 is connected to the corresponding green signal charge accumulation region through vertical wiring.

Hereinafter, the form of each layer constituting the photoelectric conversion element according to an embodiment of the present invention will be described in detail.

Photoelectric Conversion Film

<Specific Compound>

The photoelectric conversion film 12 (or the organic photoelectric conversion film 209) is a film including the specific compound as a photoelectric conversion material. By using the compound, a photoelectric conversion element having excellent heat resistance is obtained.

Hereinafter, the specific compound will be described in detail.

Formula (1) includes all geometric isomers that can be distinguished based on the C=C double bond composed of a carbon atom to which $R^2$ is bonded and a carbon atom adjacent thereto in Formula (1). That is, both the cis isomer and the trans isomer which are distinguished based on the C=C double bond are included in the compound represented by Formula (1).

The same applies to Formula (2), and Formula (2) includes all geometric isomers that can be distinguished based on the C=C double bond composed of a carbon atom to which $R^2$ is bonded and a carbon atom adjacent thereto in Formula (2).

In the present specification, unless otherwise noted, examples of substituents which can be included in the specific compound include, each independently, a group represented by Formula (C) (preferably a group represented by Formula (CX)) described later and a substituent W described later.

In addition, unless otherwise noted, examples of alkyl groups (including alkyl groups which may have a substituent) which can be included in the specific compound include, each independently, an alkyl group AL described later. Examples of aryl groups (including aryl groups which may have a substituent) include, each independently, an aryl group AR described later, and examples of heteroaryl groups (including heteroaryl groups which may have a substituent) include, each independently, a heteroaryl group HA described later.

The photoelectric conversion film included in the photoelectric conversion element according to the embodiment of the present invention includes the at least one compound selected from the group consisting of the compound represented by Formula (1) and the compound represented by Formula (2).

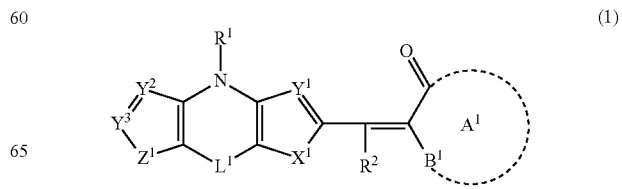

(1)

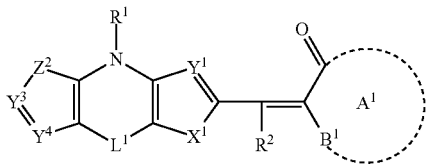

(2)

In Formulae (1) and (2), $R^1$ and $R^2$ each independently represent a hydrogen atom or a substituent.

It is preferable that $R^1$ and $R^2$ are each independently a hydrogen atom, an alkyl group which may have a substituent, an aryl group which may have a substituent, or a heteroaryl group which may have a substituent.

Among these, $R^1$ is preferably an alkyl group which may have a substituent, an aryl group which may have a substituent, or a heteroaryl group which may have a substituent, and more preferably an aryl group which may have a substituent or a heteroaryl group which may have a substituent.

$R^2$ is preferably a hydrogen atom.

In Formulae (1) and (2), $X^1$ represents a sulfur atom, an oxygen atom, a selenium atom, a tellurium atom, —$NR^{a1}$—, —$CR^{a2}R^{a3}$—, or —$SiR^{a4}R^{a5}$—.

$R^{a1}$ to $R^{a5}$ each independently represent a hydrogen atom or a substituent, and are preferably a hydrogen atom, an alkyl group which may have a substituent, an aryl group which may have a substituent, or a heteroaryl group which may have a substituent.

Among these, $X^1$ is preferably a sulfur atom, an oxygen atom, or a selenium atom, more preferably a sulfur atom or an oxygen atom, and still more preferably a sulfur atom.

$Y^1$ to $Y^4$ each independently represent —$CR^{a6}$= or a nitrogen atom.

$R^{a6}$ represents a hydrogen atom or a substituent.

Among these, it is preferable that $Y^1$ and $Y^2$, and $Y^4$ are each independently —CH= or a nitrogen atom, and it is more preferable that $Y^1$ and $Y^2$, and $Y^4$ are —CH=.

$Y^3$ is preferably —$CR^{a6}$=.

In a case where $Y^3$ is —$CR^{a6}$=, $R^{a6}$ is preferably a hydrogen atom, an alkyl group which may have a substituent, an aryl group which may have a substituent, a heteroaryl group which may have a substituent, or a group represented by Formula (C) (preferably a group represented by Formula (CX)) described later.

$L^1$ represents a single bond, an oxygen atom, a sulfur atom, a selenium atom, a tellurium atom, —$NR^{a7}$—, —$CR^{a8}R^{a9}$—, —$SiR^{a10}R^{a11}$—, or —CO—.

Among these, $L^1$ is preferably a single bond, an oxygen atom, —$CR^{a8}R^{a9}$—, —$SiR^{a10}R^{a11}$—, or —CO—, and more preferably a single bond or —$CR^{a8}R^{a9}$—.

$R^{a7}$ to $R^{a11}$ each independently represent a hydrogen atom or a substituent.

It is preferable that $R^{a7}$ to $R^{a11}$ are each independently a hydrogen atom, a halogen atom (preferably a fluorine atom), an alkyl group which may have a substituent, an aryl group which may have a substituent, or a heteroaryl group which may have a substituent, and it is more preferable that $R^{a7}$ to $R^{a11}$ are an alkyl group which may have a substituent.

The alkyl group which may have a substituent is preferably a linear or branched alkyl group having 1 to 4 carbon atoms, and more preferably a methyl group.

In addition, in a case where $L^1$ is —$CR^{a8}R^{a9}$—, it is also preferable that $R^{a8}$ and $R^{a9}$ are bonded to each other to form a ring, and in a case where $L^1$ is —$SiR^{a10}R^{a11}$—, it is also preferable that $R^{a10}$ and $R^{a11}$ are bonded to each other to form a ring. Here, the ring formed by bonding $R^{a8}$ and $R^{a9}$ (or $R^{a10}$ and $R^{a11}$) is preferably, for example, a hydrocarbon ring (preferably having 4 to 20 carbon atoms) which may have a substituent, and more preferably a saturated hydrocarbon ring (preferably 5 or 6 carbon atoms) which may have a substituent or an aromatic hydrocarbon ring (preferably having 6 to 18 carbon atoms; for example, a fluorene ring) which may have a substituent.

In a case where $L^1$ is a single bond, $Z^1$ and $Z^2$ each independently represent a sulfur atom, an oxygen atom, a selenium atom, a tellurium atom, —$NR^{a12}$—, —$CR^{a13}R^{a14}$—, —$SiR^{a15}R^{a16}$—, or —CO—.

In this case, among these, it is preferable that $Z^1$ and $Z^2$ are each independently a sulfur atom or an oxygen atom, and it is more preferable that $Z^1$ and $Z^2$ are a sulfur atom.

In addition, in this case, $R^{a12}$ to $R^{a16}$ each independently represent a hydrogen atom or a substituent, and are preferably a hydrogen atom, an alkyl group which may have a substituent, an aryl group which may have a substituent, or a heteroaryl group which may have a substituent.

In a case where $L^1$ is an oxygen atom, a sulfur atom, a selenium atom, a tellurium atom, —$NR^{a7}$—, —$CR^{a8}R^{a9}$—, —$SiR^{a10}R^{a11}$—, or —CO—, $Z^1$ and $Z^2$ each independently represent a sulfur atom, an oxygen atom, a selenium atom, a tellurium atom, —$NR^{a12}$—, —$CR^{a13}R^{a14}$—, —$SiR^{a15}R^{a16}$—, —CO—, or —$CR^{a17}$=$CR^{a18}$—.

In this case, among these, it is preferable that $Z^1$ and $Z^2$ are each independently a sulfur atom, an oxygen atom, or —$CR^{a17}$=$CR^{a18}$—, and it is more preferable that $Z^1$ and $Z^2$ are each independently a sulfur atom or —$CR^{a17}$=$CR^{a18}$—.

In addition, in this case, $R^{a12}$ to $R^{a18}$ each independently represent a hydrogen atom or a substituent, and are preferably a hydrogen atom, an alkyl group which may have a substituent, an aryl group which may have a substituent, or a heteroaryl group which may have a substituent, and more preferably a hydrogen atom.

$B^1$ represents —CO—, an oxygen atom, a sulfur atom, a selenium atom, a tellurium atom, —$NR^{a19}$—, —$CR^{a20}R^{a21}$—, or —$SiR^{a22}R^{a23}$—.

$R^{a19}$ to $R^{a23}$ each independently represent a hydrogen atom or a substituent, and are preferably a hydrogen atom, an alkyl group which may have a substituent, an aryl group which may have a substituent, or a heteroaryl group which may have a substituent.

Among these, $B^1$ is preferably —CO—, an oxygen atom, or a sulfur atom, and more preferably —CO—.

$A^1$ represents a ring.

More specifically, $A^1$ is a ring including, as specified in Formulae (1) and (2), a "carbon atom represented by =C<, which forms a vinylene group together with the carbon atom to which $R^2$ is bonded", and "—CO—" and "—$B^1$—" bonded to the carbon atom.

A preferred form of $A^1$ will be described later.

In Formula (1), $R^1$, $R^2$, and $R^{a1}$ to $R^{a23}$ may be respectively bonded to each other to form a ring.

Specifically, for example, $R^{a6}$ and $R^1$ of $Y^1$ in a case where $Y^1$ represents —$CR^{a6}$=; $R^{a6}$ and $R^2$ of $Y^1$ in a case where $Y^1$ represents —$CR^{a6}$=; $R^{a6}$ and $R^1$ of $Y^2$ in a case where $Y^2$ represents —$CR^{a6}$=; $R^{a6}$ of $Y^2$ and $R^{a6}$ of $Y^3$ in a case where $Y^2$ and $Y^3$ represent —$CR^{a6}$=; $R^{a12}$ to $R^{a18}$ of $Z^1$ and $R^{a6}$ of $Y^3$ in a case where $Z^1$ represents —$NR^{a12}$—, —$CR^{a13}R^{a14}$—, —$SIR^{a15}R^{a16}$—, or —$CR^{a17}$=$CR^{a18}$— and $Y^3$ represents —$CR^{a6}$=; $R^{a12}$ to $R^{a18}$ of $Z^1$ and $R^{a7}$ to $R^{a11}$ of $L^1$ in a case where $Z^1$ represents —$NR^{a12}$—, —$CR^{a13}R^{a14}$—, —$SIR^{a15}R^{a16}$—, or —$CR^{a17}$=$CR^{a18}$— and $L^1$ represents —$NR^{a7}$—, —$CR^{a8}R^{a9}$— or —SiR$^{a10}$R$^{a11}$—; R$^{a7}$ to R$^{a11}$ of L$^1$ and R$^{a1}$ to R$^{a5}$ of X$^1$ in a case where L$^1$ represents —NR$^{a7}$—, —CR$^{a8}$R$^{a9}$—, or —SIR$^{a10}$R$^{a11}$— and X$^1$ represents —NR$^{a1}$—, —CR$^{a2}$R$^{a3}$— or —SiR$^{a4}$R$^{a5}$—; R$^{a1}$ to R$^{a5}$ of X$^1$ and R$^2$ in a case where X$^1$ represents —NR$^{a1}$—, —CR$^{a2}$R$^{a3}$—, or —SiR$^{a4}$R$^{a5}$—; and R$^{a19}$ to R$^{a23}$ of B$^1$ and R$^2$ in a case where B$^1$ represents —NR$^{a19}$—, —CR$^{a20}$R$^{a21}$—, or —SiR$^{a22}$R$^{a23}$— may be respectively bonded to each other to form a ring.

Among these, it is preferable that, in a case where Y$^2$ and Y$^3$ represent —CR$^{a6}$=, R$^{a6}$ of Y$^2$ and R$^{a6}$ of Y$^3$ are bonded to each other to form a ring. As the ring formed by bonding R$^{a6}$ of Y$^2$ and R$^{a6}$ of Y$^3$ to each other, for example, an aromatic ring (preferably a 5- or 6-membered aromatic ring, more preferably a furan ring) is preferable, and a ring in which a substituent of the aromatic ring further forms a ring (preferably a 5- or 6-membered aromatic ring, more preferably a thiophene ring) is also preferable.

In Formula (2), R$^1$, R$^2$, and R$^{a1}$ to R$^{a23}$ may be respectively bonded to each other to form a ring.

Specifically, for example, R$^{a6}$ and R$^1$ of Y$^1$ in a case where Y$^1$ represents —CR$^{a6}$=; R$^{a6}$ and R$^2$ of Y$^1$ in a case where Y$^1$ represents —CR$^{a6}$=; R$^{a12}$ to R$^{a18}$ of Z$^2$ and R$^1$ in a case where Z$^2$ represents —NR$^{a12}$—, —CR$^{a13}$R$^{a14}$—, —SIR$^{a15}$R$^{a16}$—, or —CR$^{a17}$=CR$^{a18}$—; R$^{a12}$ to R$^{a18}$ of Z$^2$ and R$^{a6}$ of Y$^3$ in a case where Z$^2$ represents —NR$^{a12}$—, —CR$^{a13}$R$^{a14}$—, —SIR$^{a15}$R$^{a16}$—, or —CR$^{a17}$=CR$^{a18}$— and Y$^3$ represents —CR$^{a6}$=; R$^{a6}$ of Y$^3$ and R$^{a6}$ of Y$^4$ in a case where Y$^3$ and Y$^4$ represent —CR$^{a6}$=; R$^{a6}$ of Y$^4$ and R$^{a7}$ to R$^{a11}$ of L$^1$ in a case where Y$^4$ represents —CR$^{a6}$= and L$^1$ represents —NR$^{a7}$—, CR$^{a8}$R$^{a9}$—, or —SiR$^{a10}$R$^{a11}$—; R$^{a7}$ to R$^{a11}$ of L$^1$ and R$^{a1}$ to R$^{a5}$ of X$^1$ in a case where L$^1$ represents —NR$^{a7}$—, —CR$^{a8}$R$^{a9}$—, or —SIR$^{a10}$R$^{a11}$— and X$^1$ represents —NR$^{a1}$—, —CR$^{a2}$R$^{a3}$— or —SiR$^{a4}$R$^{a5}$—; R$^{a1}$ to R$^{a5}$ of X$^1$ and R$^2$ in a case where X$^1$ represents —NR$^{a1}$—, —CR$^{a2}$R$^{a3}$—, or —SiR$^{a4}$R$^{a5}$—; and R$^{a19}$ to R$^{a23}$ of B$^1$ and R$^2$ in a case where B$^1$ represents —NR$^{a19}$—, —CR$^{a20}$R$^{a21}$—, or —SiR$^{a22}$R$^{a23}$— may be respectively bonded to each other to form a ring.

Among these, it is preferable that, in a case where Y$^3$ and Y$^4$ represent —CR$^{a6}$=, R$^{a6}$ of Y$^3$ and R$^{a6}$ of Y$^4$ are bonded to each other to form a ring. As the ring formed by bonding R$^{a6}$ of Y$^3$ and R$^{a6}$ of Y$^4$ to each other, for example, an aromatic ring (preferably a 5- or 6-membered aromatic ring, more preferably a furan ring) is preferable, and a ring in which a substituent of the aromatic ring further forms a ring (preferably a 5- or 6-membered aromatic ring, more preferably a thiophene ring) is also preferable.

The number of carbon atoms of A$^1$ in Formulae (1) and (2) described above is preferably 3 to 30, more preferably 3 to 20, and still more preferably 3 to 15. The above-described number of carbon atoms is the number including the carbon atom of "—CO—", the "carbon atom represented by =C<, which forms a vinylene group together with the carbon atom to which R$^2$ is bonded", and "—B$^1$—" as specified in the formulae.

A$^1$ may have a hetero atom, and examples thereof include a nitrogen atom, a sulfur atom, an oxygen atom, a selenium atom, a tellurium atom, a phosphorus atom, a silicon atom, and a boron atom. A nitrogen atom, a sulfur atom, or an oxygen atom is preferable and an oxygen atom is more preferable.

A$^1$ may have a substituent, and the substituent is preferably a halogen atom (preferably a chlorine atom).

The number of hetero atoms in A$^1$ is preferably 0 to 10, more preferably 0 to 5, and still more preferably 0 to 2. The above-described number of hetero atoms is a number not including the number of hetero atoms included in "—CO—" and "—B$^1$—" specified in the formulae, and the number of hetero atoms included in the substituent of A$^1$.

A$^1$ may or may not indicate aromaticity.

A$^1$ may have a monocyclic structure or a condensed ring structure, but is preferably a 5-membered ring, a 6-membered ring, or a fused ring including at least any one of a 5-membered ring or a 6-membered ring. The number of rings forming the fused ring is preferably 1 to 4 and more preferably 1 to 3.

As A$^1$, a ring normally used as an acidic nucleus in a merocyanine coloring agent is preferable, and specific examples thereof include the following ring.

(a) 1,3-Dicarbonyl nucleus: for example, 1,3-indandione, 1,3-cyclohexanedione, 5,5-dimethyl-1,3-cyclohexanedione, 1,3-dioxane-4,6-dione, and the like.

(b) 2,4,6-Trioxohexahydropyrimidine nucleus: for example, barbituric acid, 2-thiobarbituric acid, derivatives thereof, and the like. Examples of the derivatives include a 1-alkyl form such as 1-methyl and 1-ethyl, a 1,3-dialkyl form such as 1,3-dimethyl, 1,3-diethyl, and 1,3-dibutyl, a 1,3-diaryl form such as 1,3-diphenyl, 1,3-di(p-chlorophenyl), 1,3-di(p-ethoxycarbonylphenyl), a 1-alkyl-1-aryl form such as 1-ethyl-3-phenyl, and a 1,3-diheteroaryl form such as 1,3-di(2-pyridyl).

(c) 2-Thio-2,4-thiazolidinedione nucleus: for example, rhodanine, derivatives thereof, and the like. Examples of the derivatives include a 3-alkylrhodanine such as 3-methylrhodanine, 3-ethylrhodanine, and 3-allylrhodanine, a 3-arylrhodanine such as 3-phenylrhodanine, and a 3-heteroaryl rhodanine such as 3-(2-pyridyl)rhodanine.

(d) 2-Thio-2,4-oxazolidinedione (2-thio-2,4-(3H,5H)-oxazoledione) nucleus: for example, 3-ethyl-2-thio-2,4-oxazolidinedione and the like.

(e) Thianaphthenone nucleus: for example, 3(2H)-thianaphthenone-1,1-dioxide and the like.

(f) 2-Thio-2,5-thiazolidinedione nucleus: for example, 3-ethyl-2-thio-2,5-thiazolidinedione and the like.

(g) 2,4-Thiazolidinedione nucleus: for example, 2,4-thiazolidinedione, 3-ethyl-2,4-thiazolidinedione, 3-phenyl-2,4-thiazolidinedione, and the like.

(h) Thiazolin-4-one nucleus: for example, 4-thiazolinone, 2-ethyl-4-thiazolinone, and the like.

(i) 2,4-Imidazolidinedione (hydantoine) nucleus: for example, 2,4-imidazolidinedione, 3-ethyl-2,4-imidazolidinedione, and the like.

(j) 2-Thio-2,4-imidazolidinedione (2-thiohydantoine) nucleus: for example, 2-thio-2,4-imidazolidinedione, 3-ethyl-2-thio-2,4-imidazolidinedione, and the like.

(k) 3,5-Pyrazolidinedione nucleus: for example, 1,2-diphenyl-3,5-pyrazolidinedione, 1,2-dimethyl-3,5-pyrazolidinedione, and the like.

(l) Indanone nucleus: for example, 1-indanone, 3-phenyl-1-indanone, 3-methyl-1-indanone, 3,3-diphenyl-1-indanone, 3,3-dimethyl-1-indanone, and the like.

(m) Benzofuran-3-(2H)-one nucleus: for example, benzofuran-3-(2H)-one and the like.

(n) 2,2-Dihydrophenalene-1,3-dione nucleus and the like.

Among these, it is preferable that A$^1$ in Formulae (1) and (2) is a ring formed from the "carbon atom represented by =C<, which forms a vinylene group together with the carbon atom to which R$^2$ is bonded", "—CO—", "—B$^1$—", and "-Q$^1$-" in Formulae (1X) and (2X), jointly.

In other words, the compounds represented by Formulae (1) and (2) are preferably compounds represented by Formulae (1X) and (2X), respectively.

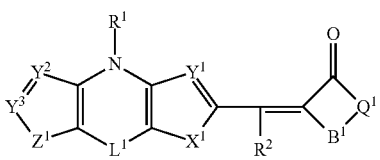

(1X)

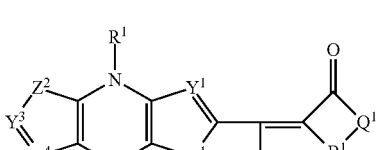

(2X)

In Formulae (1X) and (2X), $R^1$, $R^2$, $X^1$, $Y^1$ to $Y^4$, $Z^1$, $Z^2$, $L^1$, and $B^1$ respectively have the same meaning as the groups represented by the same symbols in Formulae (1) and (2).

In Formula (1X), $R^1$, $R^2$, and $R^{a1}$ to $R^{a23}$ may be respectively bonded to each other to form a ring, and in Formula (2X), $R^1$, $R^2$, and $R^{a1}$ to $R^{a23}$ may be respectively bonded to each other to form a ring.

Examples of an aspect of forming a ring are as described above.

In Formulae (1X) and (2X), $Q^1$ represents $-CR^{c1}=CR^{c2}-$, $-NR^{c3}-$, $-C(=R^{c4})-$, an ether group, or a group consisting of a combination of these groups.

$R^{c1}$ to $R^{c3}$ are each independently a hydrogen atom or a substituent, and preferably a hydrogen atom or an alkyl group (preferably having 1 to 4).

$R^{c4}$ is a divalent substituent forming a double bond with a carbon atom, and preferably an oxygen atom or a sulfur atom.

Among these, $Q^1$ is preferably $-CR^{c1}=CR^{c2}-$.

$R^{c1}$ to $R^{c4}$ may be respectively bonded to each other to form a ring.

For example, in $-CR^{c1}=CR^{c2}-$, $R^{c1}$ and $R^{c2}$ are preferably bonded to each other to form a ring, and as the formed ring, a benzene ring which may have a substituent is preferable. In addition, the substituents of the benzene ring may be bonded to each other to further form a ring.

In addition, in a case where $-CR^{c1}=CR^{c2}-$ and $-C(=R^{c4})-$ are adjacent to each other, it is also preferable that $R^{c1}$ and $R^{c2}$ are bonded to each other to form a ring, and the ring formed from $R^{c1}$ and $R^{c2}$ and $R^{c4}$ are further bonded to each other to form another ring. $Q^1$ in this case is, for example, 1,8-naphthalenediyl group.

Among these, the divalent linking group represented by $Q^1$ is preferably a divalent linking group represented by Formula (D).

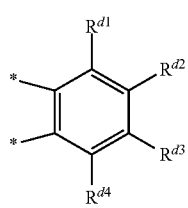

(D)

In Formula (D), * represents a bonding site.

$R^{d1}$ to $R^{d4}$ each independently represent a hydrogen atom or a substituent, and are preferably a hydrogen atom or a halogen atom (preferably a chlorine atom).

$R^{d1}$ and $R^{d2}$, $R^{d2}$ and $R^{d3}$, and $R^{d3}$ and $R^{d4}$ may be respectively bonded to each other to form a ring. Among these, it is preferable that $R^{d2}$ and $R^{d3}$ are bonded to each other to form a ring. The ring formed as described above is not particularly limited, and is preferably an aromatic ring and more preferably a benzene ring which may have a substituent.

The compound represented by Formula (1) is preferably a compound represented by Formula (3), and the compound represented by Formula (2) is preferably a compound represented by Formula (4).

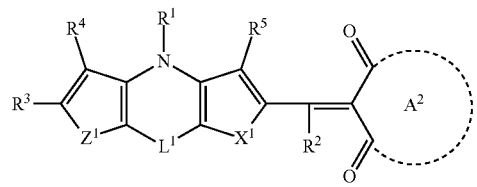

(3)

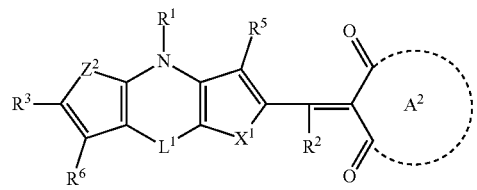

(4)

In Formulae (3) and (4), $R^1$ to $R^6$ each independently represent a hydrogen atom or a substituent.

$R^1$ and $R^2$ in Formulae (3) and (4) have the same meaning as $R^1$ and $R^2$ in Formulae (1) and (2).

$R^3$ is preferably a hydrogen atom, an alkyl group which may have a substituent, an aryl group which may have a substituent, a heteroaryl group which may have a substituent, or a group represented by Formula (C) (preferably a group represented by Formula (CX)) described later.

$R^4$ to $R^6$ are preferably hydrogen atoms.

$X^1$ represents a sulfur atom, an oxygen atom, a selenium atom, a tellurium atom, $-NR^{a1}-$, $-CR^{a2}R^{a3}-$, or $-SiR^{a4}R^{a5}-$.

$R^{a1}$ to $R^{a5}$ each independently represent a hydrogen atom or a substituent.

$X^1$ and $R^{a1}$ to $R^{a5}$ in Formulae (3) and (4) respectively have the same meaning as $X^1$ and $R^{a1}$ to $R^{a5}$ in Formulae (1) and (2).

$L^1$ represents a single bond, an oxygen atom, a sulfur atom, a selenium atom, a tellurium atom, $-NR^{a7}-$, $-CR^{a8}R^{a9}-$, $-SiR^{a10}R^{a11}-$, or $-CO-$.

$R^{a7}$ to $R^{a11}$ each independently represent a hydrogen atom or a substituent.

$L^1$ and $R^{a7}$ to $R^{a11}$ in Formulae (3) and (4) respectively have the same meaning as $L^1$ and $R^{a7}$ to $R^{a11}$ in Formulae (1) and (2).

In a case where $L^1$ is a single bond, $Z^1$ and $Z^2$ each independently represent a sulfur atom, an oxygen atom, a selenium atom, a tellurium atom, $-NR^{a12}-$, $-CR^{a13}R^{a14}-$, $-SiR^{a15}R^{a16}-$, or $-CO-$.

In a case where $L^1$ is an oxygen atom, a sulfur atom, a selenium atom, a tellurium atom, $-NR^{a7}-$, $-CR^{a8}R^{a9}-$, $-SiR^{a10}R^{a11}-$, or $-CO-$, $Z^1$ and $Z^2$ each independently represent a sulfur atom, an oxygen atom, a selenium atom, a tellurium atom, $-NR^{a12}-$, $-CR^{a13}R^{a14}-$, $-SiR^{a15}R^{a16}-$, $-CO-$, or $-CR^{a17}=CR^{a18}-$.

$R^{a12}$ to $R^{a18}$ each independently represent a hydrogen atom or a substituent.

$Z^1$, $Z^2$, and $R^{a12}$ to $R^{a18}$ in Formulae (3) and (4) respectively have the same meaning as $Z^1$, $Z^2$, and $R^{a12}$ to $R^{a18}$ in Formulae (1) and (2).

$A^2$ represents a ring.

More specifically, $A^2$ is a ring including, as specified in Formulae (3) and (4), the "carbon atom represented by =C<, which forms a vinylene group together with the carbon atom to which $R^2$ is bonded" and two "—CO—" adjacent to the carbon atom.

A preferred form of $A^2$ will be described later.

In Formula (3), $R^1$ to $R^5$, $R^{a1}$ to $R^{a5}$, and $R^{a7}$ to $R^{a18}$ may be respectively bonded to each other to form a ring.

Specifically, for example, $R^1$ and $R^5$; $R^1$ and $R^4$; $R^3$ and $R^4$; $R^2$ and $R^5$; $R^{a12}$ to $R^{a18}$ of $Z^1$ and $R^3$ in a case where $Z^1$ represents —$NR^{a12}$—, —$CR^{a13}R^{14}$—, —$SiR^{a15}R^{a16}$—, or —$CR^{a17}$=$CR^{a18}$—; $R^{a12}$ to $R^{a18}$ of $Z^1$ and $R^{a7}$ to $R^{a11}$ of $L^1$ in a case where $Z^1$ represents —$NR^{a12}$—, —$CR^{a13}R^{a14}$—, —$SIR^{a15}R^{a16}$—, or —$CR^{a17}$=$CR^{a18}$— and $L^1$ represents —$NR^{a7}$—, —$CR^{a8}R^{a9}$— or —$SiR^{a10}R^{a11}$—; $R^{a7}$ to $R^{a11}$ of $L^1$ and $R^{a1}$ to $R^{a5}$ of $X^1$ in a case where $L^1$ represents —$NR^{a7}$—, —$CR^{a8}R^{a9}$—, or —$SIR^{a10}R^{a11}$— and $X^1$ represents —$NR^{a1}$—, —$CR^{a2}R^{a3}$— or —$SiR^{a4}R^{a5}$—; and $R^{a1}$ to $R^{a5}$ of $X^1$ and $R^2$ in a case where $X^1$ represents —$NR^{a1}$—, —$CR^{a2}R^{a3}$—, or —$SiR^{a4}R^{a5}$— may be respectively bonded to each other to form a ring.

Among these, it is preferable that $R^3$ and $R^4$ are bonded to each other to form a ring. As the ring formed by bonding $R^3$ and $R^4$ to each other, for example, an aromatic ring (preferably a 5- or 6-membered aromatic ring, more preferably a furan ring) is preferable, and a ring in which a substituent of the aromatic ring further forms a ring) preferably a 5- or 6-membered aromatic ring, more preferably a thiophene ring) is also preferable.

In Formula (4), $R^1$ to $R^3$, $R^5$, $R^6$, $R^{a1}$ to $R^{a5}$, and $R^{a7}$ to $R^{a18}$ may be respectively bonded to each other to form a ring.

Specifically, for example, $R^1$ and $R^5$; $R^2$ and $R^5$; $R^3$ and $R^6$; $R^{a12}$ to $R^{a18}$ of $Z^2$ and $R^1$ in a case where $Z^2$ represents —$NR^{a12}$—, —$CR^{a13}R^{a14}$—, —$SiR^{a15}R^{a16}$—, or —$CR^{a17}$=$CR^{a18}$—; $R^{a12}$ to $R^{a18}$ of $Z^2$ and $R^3$ in a case where $Z^2$ represents —$NR^{a12}$—, —$CR^{a13}R^{a14}$—, —$SIR^{a15}R^{a16}$—, or —$CR^{a17}$=$CR^{a18}$—; $R^{a7}$ to $R^{a11}$ of $L^1$ and $R^6$ in a case where $L^1$ represents —$NR^{a7}$—, —$CR^{a8}R^{a9}$—, or —$SIR^{a10}R^{a11}$— and $X^1$ represents —$NR^{a1}$—, —$CR^{a2}R^{a3}$— or —$SiR^{a4}R^{a5}$—; $R^{a7}$ to $R^{a11}$ of $L^1$ and $R^{a1}$ to $R^{a5}$ of $X^1$ in a case where $L^1$ represents —$NR^{a7}$—, —$CR^{a8}R^{a9}$—, or —$SIR^{a10}R^{a11}$— and $X^1$ represents —$NR^{a1}$—, —$CR^{a2}R^{a3}$— or —$SiR^{a4}R^{a5}$—; and $R^{a1}$ to $R^{a5}$ of $X^1$ and $R^2$ in a case where $X^1$ represents —$NR^{a1}$—, —$CR^{a2}R^{a3}$—, or —$SiR^{a4}R^{a5}$— may be respectively bonded to each other to form a ring.

Among these, it is preferable that $R^3$ and $R^6$ are bonded to each other to form a ring. As the ring formed by bonding $R^3$ and $R^6$ to each other, for example, an aromatic ring (preferably a 5- or 6-membered aromatic ring, more preferably a furan ring) is preferable, and a ring in which a substituent of the aromatic ring further forms a ring (preferably a 5- or 6-membered aromatic ring, more preferably a thiophene ring) is also preferable.

$A^2$ in Formulae (3) and (4) corresponds to $A^1$ in Formulae (1) and (2) in a case where $B^1$ represents —CO—.

Examples of a preferred aspect of $A^2$ include the same preferred aspect of $A^1$ in Formulae (1) and (2) in a case where $B^1$ represents —CO—.

That is, it is preferable that $A^2$ in Formulae (3) and (4) is a ring formed from the "carbon atom represented by =C<, which forms a vinylene group together with the carbon atom to which $R^2$ is bonded", two "—CO—", and "-$Q^1$-" in Formulae (3X) and (4X), jointly.

In other words, the compounds represented by Formulae (3) and (4) are preferably compounds represented by Formulae (3X) and (4X), respectively.

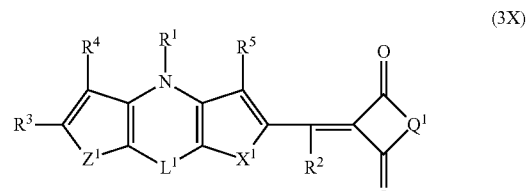

(3X)

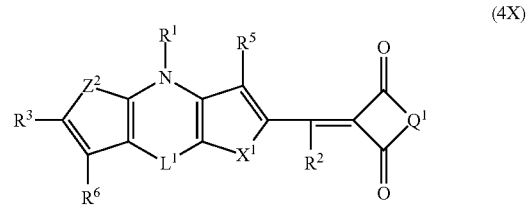

(4X)

In Formulae (3X) and (4X), $R^1$ to $R^6$, $X^1$, $Z^1$, $Z^2$, and $L^1$ have the same meaning as the groups represented by the same symbols in Formulae (3) and (4).

In Formula (3X), $R^1$ to $R^5$, $R^{a1}$ to $R^{a5}$, and $R^{a7}$ to $R^{a18}$ may be respectively bonded to each other to form a ring, and in Formula (4X), $R^1$ to $R^3$, $R^5$, $R^6$, $R^{a1}$ to $R^{a5}$, and $R^{a7}$ to $R^{a18}$ may be respectively bonded to each other to form a ring.

Examples of an aspect of forming a ring are as described above.

$Q^1$ has the same meaning as $Q^1$ in Formulae (1X) and (2X).

Among these, the specific compound is preferably a compound represented by Formula (5).

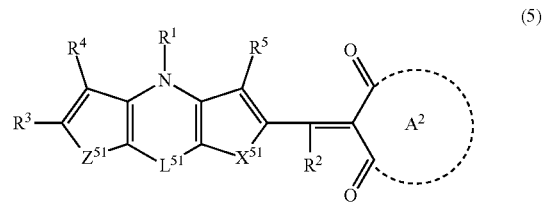

(5)

In Formula (5), $R^1$ to $R^5$ each independently represent a hydrogen atom or a substituent.

$R^1$ to $R^5$ in Formula (5) have the same meaning as $R^1$ to $R^5$ in Formula (3).

$X^{51}$ represents a sulfur atom or an oxygen atom.

$X^{51}$ is preferably a sulfur atom.

$L^{51}$ represents a single bond or —$CR^{a51}R^{a52}$—.

$R^{a51}$ and $R^{a52}$ each independently represent a hydrogen atom or a substituent.

$R^{a51}$ and $R^{a52}$ respectively have the same meaning as $R^{a8}$ and $R^{a9}$ in Formula (1).

$R^{a51}$ and $R^{a52}$ may be bonded to each other to form a ring, and examples of an aspect of forming the ring include the same aspect of forming a ring by bonding $R^{a8}$ and $R^{a9}$ to each other.

In a case where $L^{51}$ is a single bond, $Z^{51}$ represents a sulfur atom or an oxygen atom.

In this case, $Z^{51}$ is preferably a sulfur atom.

In a case where $L^{51}$ is $-CR^{a51}R^{a52}-$, $Z^{51}$ represents a sulfur atom, an oxygen atom, or $-CR^{a53}=CR^{a54}-$.

In this case, $Z^{51}$ is preferably a sulfur atom or $-CR^{a53}=CR^{a54}-$.

$R^{a53}$ and $R^{a54}$ each independently represent a hydrogen atom or a substituent.

$R^{a53}$ and $R^{a54}$ respectively have the same meaning as $R^{a17}$ and $R^{a18}$ in Formula (1).

$A^2$ represents a ring.

$A^2$ in Formula (5) have the same meaning as $A^2$ in Formula (3).

A preferred form of $A^2$ will be described later.

$R^1$ to $R^5$, and $R^{a51}$ to $R^{a54}$ may be respectively bonded to each other to form a ring.

Specifically, for example, $R^1$ and $R^5$; $R^1$ and $R^4$; $R^3$ and $R^4$; $R^2$ and $R^5$; $R^{a53}$ and $R^{a54}$ of $Z^{51}$ and $R^3$ in a case where $Z^{51}$ represents $-CR^{a53}=CR^{a54}-$; and $R^{a53}$ and $R^{a54}$ of $Z^{51}$ and $R^{a51}$ and $R^{a52}$ of $L^{51}$ in a case where $Z^{51}$ represents $-CR^{a53}=CR^{a54}-$ and $L^{51}$ represents $-CR^{a51}R^{a52}-$ may be respectively bonded to each other to form a ring.

Among these, it is preferable that $R^3$ and $R^4$ are bonded to each other to form a ring. A preferred form of the ring formed by bonding $R^3$ and $R^4$ to each other is as described above in the description of Formula (3).

It is preferable that $A^2$ in Formula (5) is a ring formed from the "carbon atom represented by =C<, which forms a vinylene group together with the carbon atom to which $R^2$ is bonded", two "—CO—", and "-$Q^1$-" in Formula (5X), jointly.

In other words, the compound represented by Formula (5) is preferably a compound represented by Formula (5X).

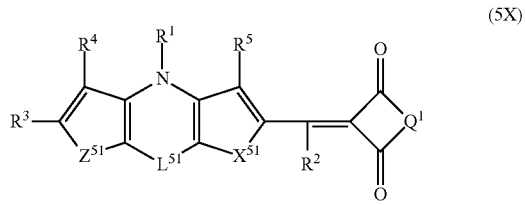

(5X)

In Formula (5X), $R^1$ to $R^5$, $X^{51}$, $Z^{51}$, and $L^{51}$ have the same meaning as the groups represented by the same symbols in Formula (5).

In Formula (5X), $R^1$ to $R^5$, and $R^{a51}$ to $R^{a54}$ may be respectively bonded to each other to form a ring.

Examples of an aspect of forming a ring are as described above.

$Q^1$ has the same meaning as $Q^1$ in Formulae (1X) and (2X).

The specific compound is more preferably a compound represented by Formula (6).

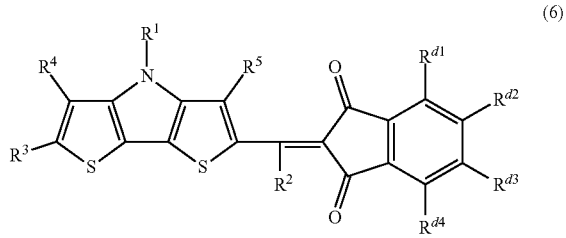

(6)

In Formula (6), $R^1$ to $R^5$, and $R^{d1}$ to $R^{d4}$ each independently represent a hydrogen atom or a substituent.

$R^1$ to $R^5$ in Formula (6) have the same meaning as $R^1$ to $R^5$ in Formula (3).

$R^{d1}$ to $R^{d4}$ in Formula (6) have the same meaning as $R^{d1}$ to $R^{d4}$ in Formula (D).

Any combination of groups selected from the group consisting of $R^1$ to $R^5$ and $R^{d1}$ to $R^{d4}$ may be respectively bonded to each other to form a ring.

Specifically, for example, $R^1$ and $R^5$, $R^1$ and $R^4$, $R^3$ and $R^4$, and $R^2$ and $R^5$ may be respectively bonded to each other to form a ring.

Among these, it is preferable that $R^3$ and $R^4$ are bonded to each other to form a ring. The ring formed by bonding $R^3$ and $R^4$ to each other is as described above in the description of Formula (3).

In addition, for example, $R^{d1}$ and $R^{d2}$, $R^{d2}$ and $R^{d3}$, and $R^{d3}$ and $R^{d4}$ may be respectively bonded to each other to form a ring, and a preferred form of such a formed ring is as described above in the description of Formula (D).

(Substituent W)

The substituent W in the present specification will be described below.

Examples of the substituent W include a halogen atom (a fluorine atom, a chlorine atom, a bromine atom, an iodine atom, and the like), an alkyl group, an alkenyl group (including a cycloalkenyl group and a bicycloalkenyl group), an alkynyl group, an aryl group, a heterocyclic group (including a heteroaryl group), a cyano group, a hydroxy group, a nitro group, an alkoxy group, an aryloxy group, a silyloxy group, a heterocyclic oxy group, an acyloxy group, a carbamoyloxy group, an alkoxycarbonyloxy group, an aryloxycarbonyloxy group, an amino group (including an anilino group), an ammonium group, an acylamino group, an aminocarbonylamino group, an alkoxycarbonylamino group, an aryloxycarbonylamino group, a sulfamoylamino group, an alkyl- or arylsulfonylamino group, a mercapto group, an alkylthio group, an arylthio group, a heterocyclic thio group, a sulfamoyl group, an alkyl- or arylsulfinyl group, an alkyl- or arylsulfonyl group, an acyl group, an aryloxycarbonyl group, an alkoxycarbonyl group, a carbamoyl group, an aryl- or heterocyclic azo group, an imide group, a phosphino group, a phosphinyl group, a phosphinyloxy group, a phosphinylamino group, a phosphono group, a silyl group, a hydrazino group, a ureido group, a boronic acid group ($-B(OH)_2$), a sulfo group, a carboxy group, a phosphoric acid group, a phosphonyl group, a phosphoryl group, a monosulfate group, a monophosphate group, a phosphonic acid group, a phosphinic acid group, a boric acid group, and other known substituents.

In addition, the substituent W may be further substituted with the substituent W. For example, an alkyl group may be substituted with a halogen atom.

The details of the substituent W are disclosed in paragraph [0023] of JP2007-234651A.

In addition, it is also preferable that, as the substituent, the specific compound has a group (preferably a group represented by Formula (CX)) represented by Formula (C).

In Formula (C), $R^2$, $B^1$, and $A^1$ have the same meaning as $R^2$, $B^1$, and $A^1$ in Formulae (1) and (2). * represents a bonding site.

In Formula (CX), $R^2$, $B^1$, and $Q^1$ have the same meaning as $R^2$, $B^1$, and $Q^1$ in Formulae (1X) and (2X). * represents a bonding site.

Formulae (C) and (CX) respectively include all geometric isomers that can be distinguished based on the C=C double bond composed of a carbon atom to which R² is bonded and a carbon atom adjacent thereto in Formulae (C) and (CX).

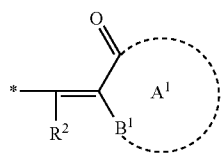

(C)

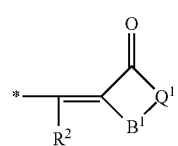

(CX)

(Alkyl Group AL)

In an alkyl group AL, the number of carbon atoms is, for example, preferably 1 to 15, more preferably 1 to 10, and still more preferably 1 to 6. The alkyl group may be linear, branched, or cyclic.

Examples of the alkyl group include a methyl group, an ethyl group, an n-propyl group, an i-propyl group, an n-butyl group, a t-butyl group, an n-hexyl group, and a cyclopentyl group.

In addition, for example, the alkyl group may be a cycloalkyl group, a bicycloalkyl group, or a tricycloalkyl group, and may have a cyclic structure thereof as a partial structure.

A substituent which can be included in the alkyl group is not particularly limited, and examples thereof include the substituent W. An aryl group (preferably having 6 to 18 carbon atoms, and more preferably having 6 carbon atoms), a heteroaryl group (preferably having 5 to 18 carbon atoms, and more preferably having 5 to 6 carbon atoms), or a halogen atom (preferably a fluorine atom or a chlorine atom) is preferable.

(Aryl Group AR)

Examples of an aryl group AR include an aryl group having 6 to 18 carbon atoms.

The aryl group may be monocyclic or polycyclic.

As an aryl group, for example, a phenyl group, a naphthyl group, or an anthryl group is preferable, and a phenyl group is more preferable.

A substituent which can be included in the aryl group is not particularly limited, and examples thereof include the substituent W. Among these, as the substituent, an alkyl group (preferably having 1 to 10 carbon atoms) which may further have a substituent is preferable, and a methyl group is more preferable.

(Heteroaryl Group HA)

Examples of a heteroaryl group HA include a heteroaryl group having a monocyclic or polycyclic ring structure including a hetero atom such as a sulfur atom, an oxygen atom, or a nitrogen atom.

The number of carbon atoms in the heteroaryl group is not particularly limited, and is preferably 3 to 18 and more preferably 3 to 5.

The number of hetero atoms included in the heteroaryl group is not particularly limited, and is preferably 1 to 10, more preferably 1 to 4, and still more preferably 1 and 2.

The number of ring members of the heteroaryl group is not particularly limited, and is preferably 3 to 8, more preferably 5 to 7, and still more preferably 5 and 6.

Examples of the heteroaryl group include a furyl group, a pyridyl group, a quinolyl group, an isoquinolyl group, an acridinyl group, a phenanthridinyl group, a pteridinyl group, a pyrazinyl group, a quinoxalinyl group, a pyrimidinyl group, a quinazolyl group, a pyridazinyl group, a cinnolinyl group, a phthalazinyl group, a triazinyl group, an oxazolyl group, a benzoxazolyl group, a thiazolyl group, a benzothiazolyl group, an imidazolyl group, a benzimidazolyl group, a pyrazolyl group, an indazolyl group, an isoxazolyl group, a benzisoxazolyl group, an isothiazolyl group, a benzisothiazolyl group, an oxadiazolyl group, a thiadiazolyl group, a triazolyl group, a tetrazolyl group, a benzofuryl group, a thienyl group, a benzothienyl group, a dibenzofuryl group, a dibenzothienyl group, a pyrrolyl group, an indolyl group, an imidazopyridinyl group, and a carbazolyl group.

A substituent which can be included in the heteroaryl group is not particularly limited, and examples thereof include the substituent W.

From the viewpoint of avoiding the deterioration of vapor deposition suitability, it is preferable that the specific compound includes neither an acidic group nor salts thereof. This is because these groups may cause decomposition of the compound during vapor deposition.

In the present specification, the "acidic group" is a substituent having a dissociative proton, and means a substituent having a pKa of 11 or less. The pKa of the acidic group is obtained according to the method "SMD/M05-2X/6-31G*" disclosed in J. Phys. Chem. A2011, 115, p. 6641 to 6645. Examples of the acidic group include acidic groups such as a carboxy group, a phosphonyl group, a phosphoryl group, a sulfo group, and a boric acid group, and groups having these acid groups.

The specific compound is exemplified below.

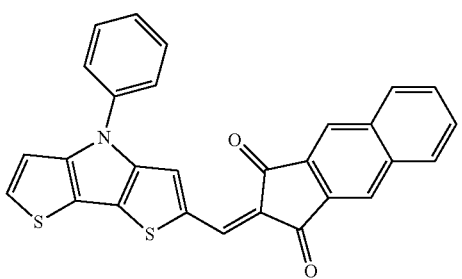

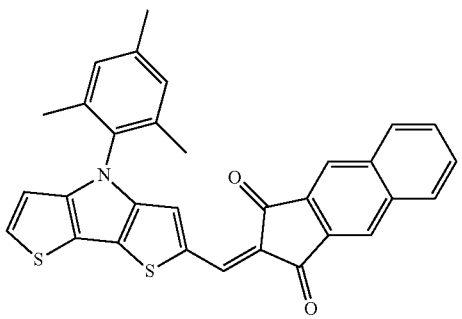

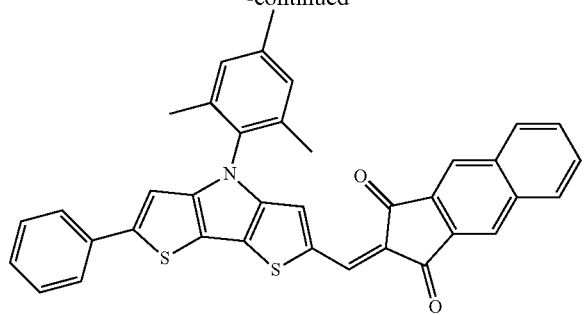
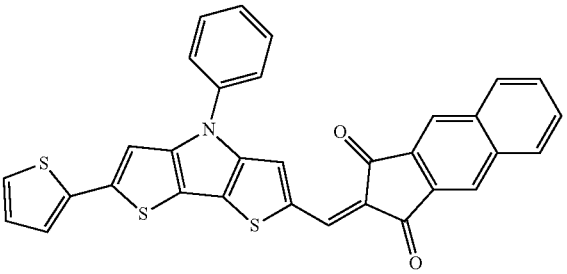
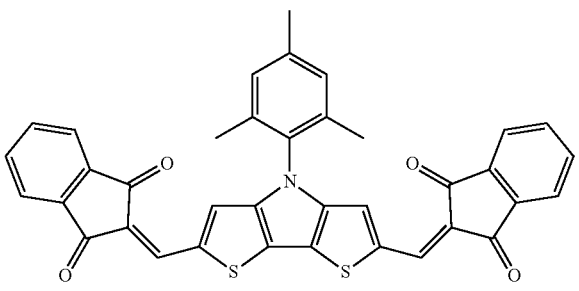
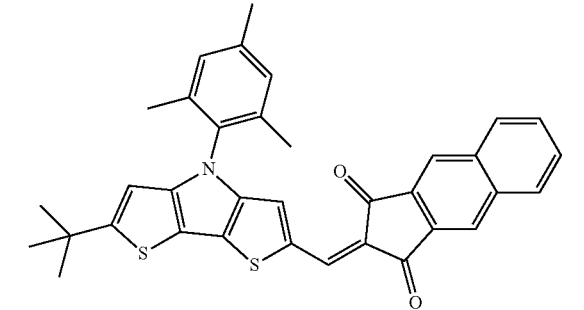
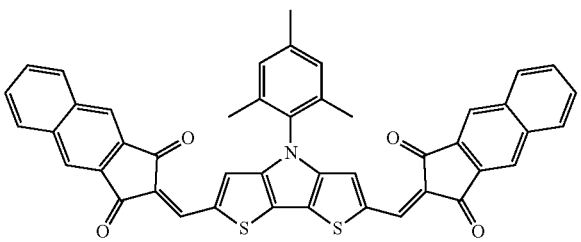
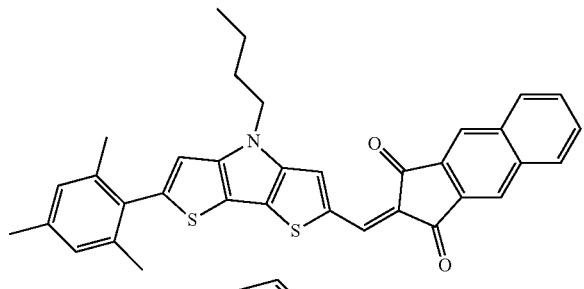
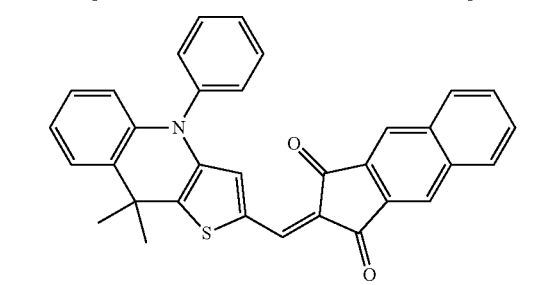
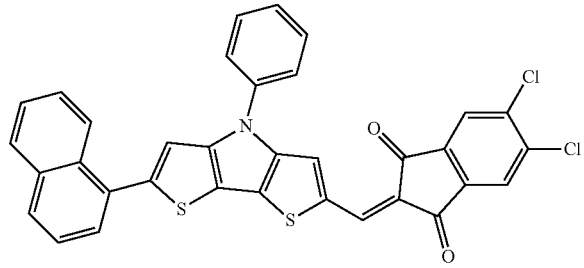
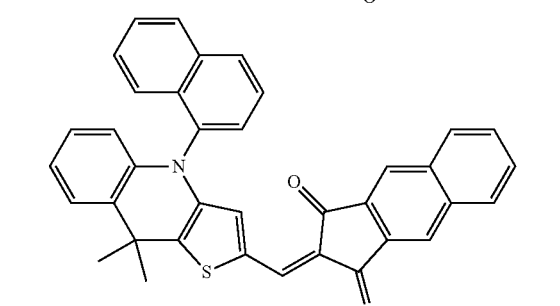
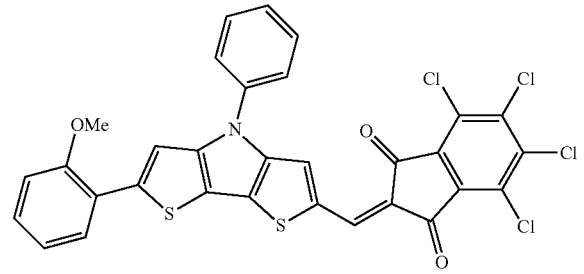
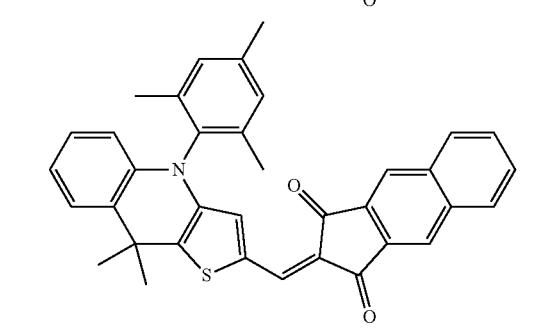

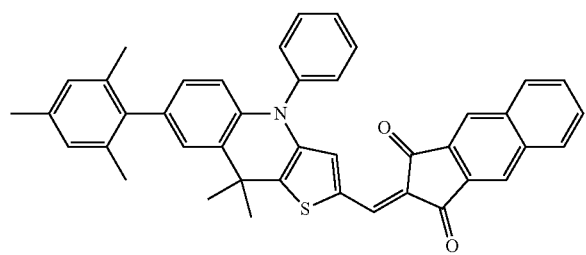
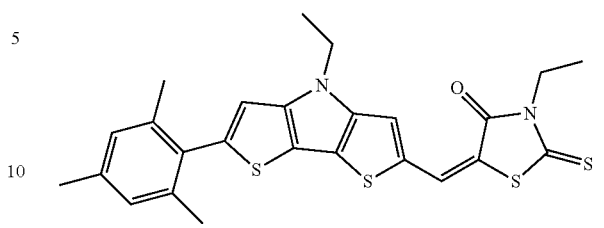
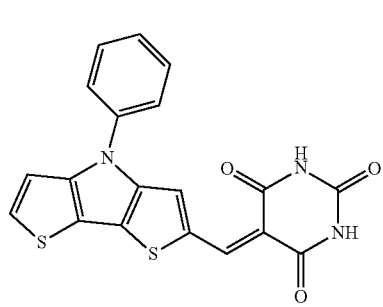
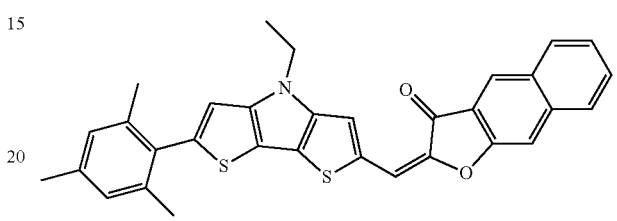
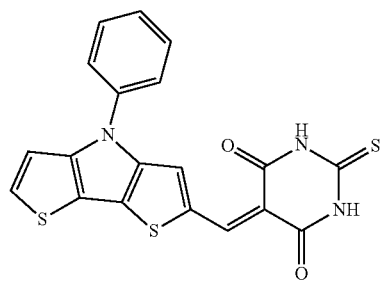
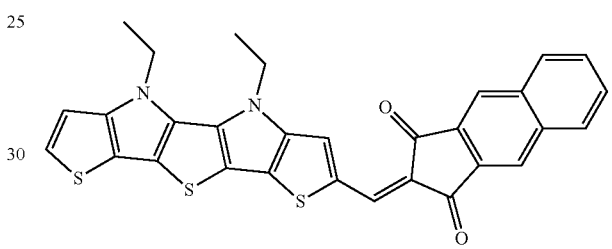
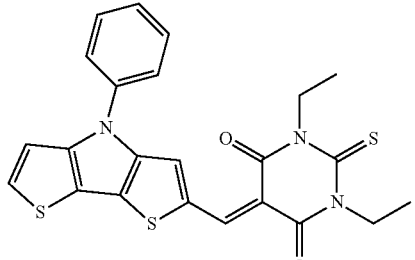
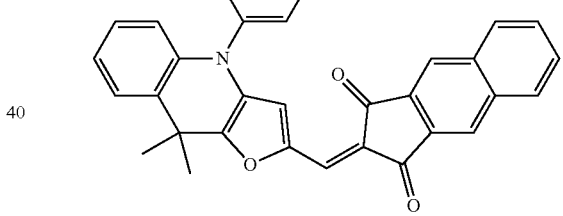
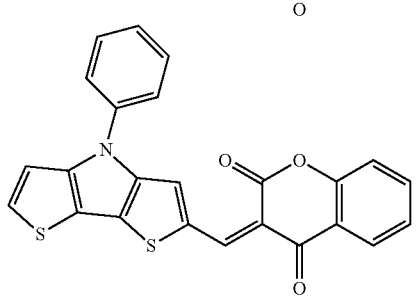
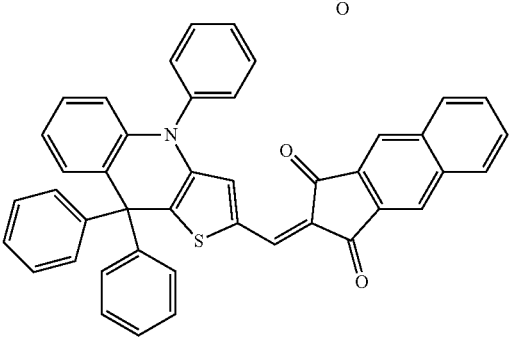
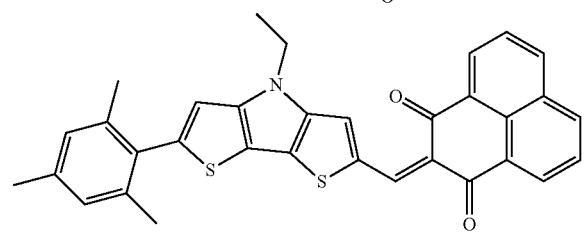
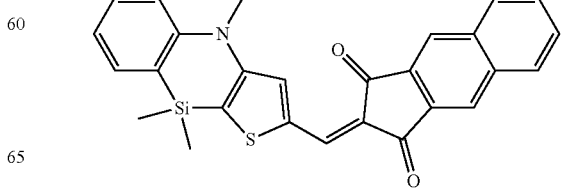

-continued

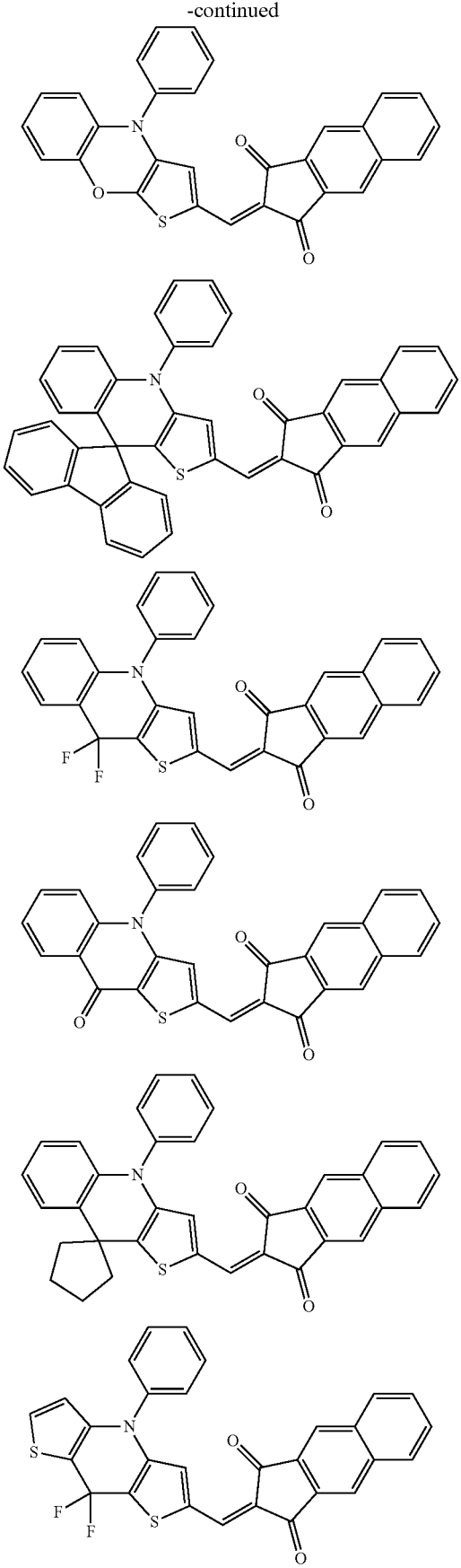

-continued

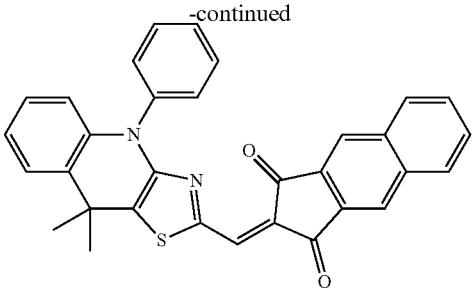

A molecular weight of the specific compound is not particularly limited, and is preferably 400 to 900. In a case where the molecular weight is 900 or less, the vapor deposition temperature does is not high, and the decomposition of the compound hardly occurs. In a case where the molecular weight is 400 or more, the glass transition point of a deposited film is not low, and heat resistance of the photoelectric conversion element is improved.

The specific compound is particularly useful as a material of the photoelectric conversion film used for an optical sensor, an imaging element, or a photoelectric cell. In addition, the specific compound usually functions as the p-type organic semiconductor in the photoelectric conversion film in many cases. The specific compound can also be used as a coloring material, a liquid crystal material, an organic semiconductor material, a charge transport material, a pharmaceutical material, and a fluorescent diagnostic material.

The specific compound is preferably a compound in which an ionization potential in a single film is −5.0 to −6.0 eV from the viewpoints of stability in a case of using the compound as the p-type organic semiconductor and matching of energy levels between the compound and the n-type organic semiconductor.

In order to be applicable to the organic photoelectric conversion film 209 which absorbs green light and performs photoelectric conversion, the maximum absorption wavelength of the specific compound is preferably in the range of 450 to 600 nm, and is more preferably in the range of 480 to 600 nm.

The maximum absorption wavelength is a value measured in a solution state (solvent:chloroform) by adjusting the absorption spectrum of the specific compound to a concentration such that the light absorbance is 0.5 to 1.

The specific compound may be used alone, or by a combination of two or more types thereof.

<n-Type Organic Semiconductor>

It is preferable that the photoelectric conversion film includes the n-type organic semiconductor as a component other than the specific compound.

The n-type organic semiconductor is an acceptor organic semiconductor material (compound), and refers to an organic compound having a property of easily accepting an electron. More specifically, the n-type organic semiconductor refers to an organic compound having a larger electron affinity of two organic compounds in a case of using the both in contact with each other.

Examples of the n-type organic semiconductor include a condensed aromatic carbocyclic compound (for example, fullerene, a naphthalene derivative, an anthracene derivative, a phenanthrene derivative, a tetracene derivative, a pyrene derivative, a perylene derivative, and a fluoranthene derivative); a 5- to 7-membered heterocyclic compound having at least one of a nitrogen atom, an oxygen atom, or a sulfur atom (for example, pyridine, pyrazine, pyrimidine, pyridazine, triazine, quinoline, quinoxaline, quinazoline, phthalazine, cinnoline, isoquinoline, pteridine, acridine, phenazine, phenanthroline, tetrazole, pyrazole, imidazole, and thiazole); a polyarylene compound; a fluorene compound; a cyclopentadiene compound; a silyl compound; and a metal complex having a nitrogen-containing heterocyclic compound as the ligands.

An organic coloring agent may be used as the n-type organic semiconductor. Examples of the organic coloring agent include a cyanine coloring agent, a styryl coloring agent, a hemicyanine coloring agent, a merocyanine coloring agent (including zeromethine merocyanine (simple merocyanine)), a rhodacyanine coloring agent, an allopolar coloring agent, an oxonol coloring agent, a hemioxonol coloring agent, a squarylium coloring agent, a croconium coloring agent, an azamethine coloring agent, a coumarin coloring agent, an arylidene coloring agent, an anthraquinone coloring agent, a triphenylmethane coloring agent, an azo coloring agent, an azomethine coloring agent, a metallocene coloring agent, a fluorenone coloring agent, a flugide coloring agent, a perylene coloring agent, a phenazine coloring agent, a phenothiazine coloring agent, a quinone coloring agent, a diphenylmethane coloring agent, a polyene coloring agent, an acridine coloring agent, an acridinone coloring agent, a diphenylamine coloring agent, a quinophthalone coloring agent, a phenoxazine coloring agent, a phthaloperylene coloring agent, a dioxane coloring agent, a porphyrin coloring agent, a chlorophyll coloring agent, a phthalocyanine coloring agent, a subphthalocyanine coloring agent, and a metal complex coloring agent.

The molecular weight of the n-type organic semiconductor is preferably 200 to 1200 and more preferably 200 to 900.

On the other hand, in a case of the form as shown in FIG. 2, it is desirable that the n-type organic semiconductor is colorless, or has a maximum absorption wavelength and/or an absorption waveform close to that of the specific compound, and a specific value of the maximum absorption wavelength of the n-type organic semiconductor is desirably 400 nm or less, or 500 to 600 nm.

The n-type organic semiconductor may be used alone, or by a combination of two or more types thereof.

It is preferable that the photoelectric conversion film has a bulk hetero structure formed in a state in which the specific compound and the n-type organic semiconductor are mixed with each other. The bulk hetero structure refers to a layer in which the specific compound and the n-type organic semiconductor are mixed and dispersed in the photoelectric conversion film. The photoelectric conversion film having the bulk hetero structure can be formed by either a wet method or a dry method. The bulk hetero structure is described in detail in, for example, paragraphs [0013] and [0014] of JP2005-303266A.

The content of the specific compound to the total content of the specific compound and the n-type organic semiconductor (=film thickness in terms of single layer of specific compound/(film thickness in terms of single layer of specific compound+film thickness in terms of single layer of n-type organic semiconductor)×100) is preferably 20 to 80 volume %, more preferably 30 to 70 volume %, and still more preferably 40 to 60 volume % from the viewpoint of responsiveness of the photoelectric conversion element.

The total content of the specific compound and the n-type organic semiconductor in the photoelectric conversion film is preferably 60 to 100 mass %.

In addition, the photoelectric conversion film may further include other components in addition to the specific compound and the n-type organic semiconductor. The types of the other components are not particularly limited, and examples thereof include a p-type organic semiconductor other than the specific compound.

In addition to the specific compound and the n-type organic semiconductor exemplified above, examples of components included in the photoelectric conversion film include a compound exemplified as an electron donating compound described later and a compound exemplified as an electron accepting compound described later.

In addition, the total number of components substantially included in the photoelectric conversion film is preferably 2 to 5 and more preferably 2 or 3.

Here, at the time of calculating the total number of components, in a case where components are included in the same classification but are different compounds, the components are separately counted as one type. For example, in a case where the photoelectric conversion film includes two types of specific compounds among the specific compounds exemplified above, each specific compound is separately counted as one type.

However, in the specific compound, regarding the cis isomer and the trans isomer which are distinguished based on the C=C double bond composed of a carbon atom to which the group represented by $R^2$ is bonded and a carbon atom adjacent thereto, the isomers are not respectively counted as a separate component.

In addition, the component substantially included in the photoelectric conversion film means a component included in the photoelectric conversion film in an amount of 1 mass % or more with respect to the total mass of the photoelectric conversion film.

The photoelectric conversion film including the specific compound is a non-luminescent film, and has a feature different from an organic light emitting diode (OLED). The non-luminescent film means a film having a luminescence quantum efficiency of 1% or less, and the luminescence quantum efficiency is preferably 0.5% or less and more preferably 0.1% or less.

<Film Formation Method>

The photoelectric conversion film can be formed mostly by a dry film formation method. Specific examples of the dry film formation method include a physical vapor deposition method such as a vapor deposition method (in particular, a vacuum evaporation method), a sputtering method, an ion plating method, and molecular beam epitaxy (MBE), and chemical vapor deposition (CVD) such as plasma polymerization. Among these, a vacuum evaporation method is preferable. In a case where the photoelectric conversion film is formed by the vacuum evaporation method, producing conditions such as a degree of vacuum and a vapor deposition temperature can be set according to the normal method.

The thickness of the photoelectric conversion film is preferably 10 to 1000 nm, more preferably 50 to 800 nm, still more preferably 50 to 500 nm, and particularly preferably 50 to 300 nm.

Electrode

The electrode (the upper electrode (the transparent conductive film) 15 and the lower electrode (the conductive film) 11) is composed of a conductive material. Examples of the conductive material include metals, alloys, metal oxides, electrically conductive compounds, and mixtures thereof.

Since light is incident through the upper electrode 15, the upper electrode 15 is preferably transparent to light to be detected. Examples of the material composing the upper electrode 15 include conductive metal oxides such as tin oxide (ATO, FTO) doped with antimony, fluorine, or the like, tin oxide, zinc oxide, indium oxide, indium tin oxide (ITO), and indium zinc oxide (IZO); metal thin films such as gold, silver, chromium, and nickel; mixtures or laminates of these metals and the conductive metal oxides; and organic conductive materials such as polyaniline, polythiophene, and polypyrrole. Among these, conductive metal oxides are preferable from the viewpoints of high conductivity, transparency, and the like.

In general, in a case where the conductive film is made to be thinner than a certain range, a resistance value is rapidly increased. However, in the solid-state imaging element into which the photoelectric conversion element according to the present embodiment is incorporated, the sheet resistance is preferably 100 to 10000Ω/□, and the degree of freedom of the range of the film thickness that can be thinned is large. In addition, as the thickness of the upper electrode (the transparent conductive film) 15 is thinner, the amount of light that the upper electrode absorbs becomes smaller, and the light transmittance usually increases. The increase in the light transmittance causes an increase in light absorbance in the photoelectric conversion film and an increase in the photoelectric conversion ability, which is preferable. Considering the suppression of leakage current, an increase in the resistance value of the thin film, and an increase in transmittance accompanied by the thinning, the film thickness of the upper electrode 15 is preferably 5 to 100 nm and more preferably 5 to 20 nm.

There is a case where the lower electrode 11 has transparency or an opposite case where the lower electrode does not have transparency and reflects light, depending on use. Examples of a material constituting the lower electrode 11 include conductive metal oxides such as tin oxide (ATO, FTO) doped with antimony, fluorine, or the like, tin oxide, zinc oxide, indium oxide, indium tin oxide (ITO), and indium zinc oxide (IZO); metals such as gold, silver, chromium, nickel, titanium, tungsten, and aluminum, conductive compounds (for example, titanium nitride (TiN)) such as oxides or nitrides of these metals; mixtures or laminates of these metals and conductive metal oxides; and organic conductive materials such as polyaniline, polythiophene, and polypyrrole.

The method of forming electrodes is not particularly limited, and can be appropriately selected in accordance with the electrode material. Specific examples thereof include a wet method such as a printing method and a coating method; a physical method such as a vacuum evaporation method, a sputtering method, and an ion plating method; and a chemical method such as a CVD method and a plasma CVD method.

In a case where the material of the electrode is ITO, examples thereof include an electron beam method, a sputtering method, a resistance thermal vapor deposition method, a chemical reaction method (such as a sol-gel method), and a coating method with a dispersion of indium tin oxide.

Charge Blocking Film: Electron Blocking Film and Positive Hole Blocking Film

It is also preferable that the photoelectric conversion element according to the embodiment of the present invention has one or more interlayers between the conductive film and the transparent conductive film, in addition to the photoelectric conversion film. Examples of the interlayer include a charge blocking film. In the case where the photoelectric conversion element has the film, the characteristics (such as an ability to suppress dark current) of the photoelectric conversion element to be obtained is more excellent. Examples of the charge blocking film include an electron blocking film and a positive hole blocking film. Hereinafter, each film will be described in detail.

<Electron Blocking Film>

The electron blocking film includes an electron donating compound. Specific examples of a low molecular material include aromatic diamine compounds such as N,N'-bis(3-methylphenyl)-(1,1'-biphenyl)-4,4'-diamine (TPD) and 4,4'-bis[N-(naphthyl)-N-phenyl-amino]biphenyl (α-NPD); porphyrin compounds such as porphyrin, copper tetraphenylporphyrin, phthalocyanine, copper phthalocyanine, and titanium phthalocyanine oxide; thienoacene compounds such as [1]benzothieno[3,2-b][1]benzothiophene (BTBT), dinaphtho [2,3-b:2',3'-f]thieno[3,2-b]thiophene (DNTT), and benzo[1,2-b:4,5-b']dithiophene (BDT); acene compounds such as tetracene, pentacene, and rubrene; phenacene compounds such as chrysene and phenanthrene; and oxazole, oxadiazole, triazole, imidazole, imidazolone, a stilbene derivative, a pyrazoline derivative, tetrahydroimidazole, polyarylalkane, butadiene, 4,4',4"-tris(N-(3-methylphenyl)-N-phenylamino) triphenylamine (m-MTDATA), a triazole derivative, an oxadiazole derivative, an imidazole derivative, a polyarylalkane derivative, a pyrazoline derivative, a pyrazolone derivative, a phenylenediamine derivative, an arylamine derivative, an amino-substituted chalcone derivative, an oxazole derivative, a styrylanthracene derivative, a fluorenone derivative, a hydrazone derivative, and a silazane derivative. Specific examples of a polymer material include a polymer such as phenylenevinylene, fluorene, carbazole, indole, pyrene, pyrrole, picoline, thiophene, acetylene, and diacetylene, and a derivative thereof. In addition, compounds described in paragraphs [0044] to [0051] of JP6047109B, compounds described in paragraphs [0049] to [0063] of JP5597450B, compounds described in paragraphs [0119] to [0158] of JP2011-225544A, and compounds described in paragraphs [0086] to [0090] of JP2012-094660A are exemplified.

The electron blocking film may be configured by a plurality of films.

The electron blocking film may be formed of an inorganic material. In general, an inorganic material has a dielectric constant larger than that of an organic material. Therefore, in a case where the inorganic material is used in the electron blocking film, a large voltage is applied to the photoelectric conversion film. Therefore, the photoelectric conversion efficiency increases. Examples of the inorganic material that can be used in the electron blocking film include calcium oxide, chromium oxide, copper chromium oxide, manganese oxide, cobalt oxide, nickel oxide, copper oxide, copper gallium oxide, copper strontium oxide, niobium oxide, molybdenum oxide, copper indium oxide, silver indium oxide, and iridium oxide.

<Positive Hole Blocking Film>

The positive hole blocking film includes an electron accepting compound.

Examples of the electron accepting compound include an oxadiazole derivative such as 1,3-bis(4-tert-butylphenyl-1, 3,4-oxadiazolyl)phenylene (OXD-7); an anthraquinodimethane derivative; a diphenylquinone derivative; bathocuproine, bathophenanthroline, and derivatives thereof; a triazole compound; a tris(8-hydroxyquinolinato)aluminum complex; a bis(4-methyl-8-quinolinato)aluminum complex; a distyrylarylene derivative; and a silole compound. In addition, compounds described in paragraphs [0056] and [0057] of JP2006-100767A are exemplified.

The method of producing the charge blocking film is not particularly limited, and examples thereof include a dry film formation method and a wet film formation method. Examples of the dry film formation method include a vapor deposition method and a sputtering method. The vapor deposition method may be any of physical vapor deposition (PVD) method and chemical vapor deposition (CVD) method, and physical vapor deposition method such as vacuum evaporation method is preferable. Examples of the wet film formation method include an inkjet method, a spray method, a nozzle printing method, a spin coating method, a dip coating method, a casting method, a die coating method, a roll coating method, a bar coating method, and a gravure coating method, and an inkjet method is preferable from the viewpoint of high-precision patterning.

Each thickness of the charge blocking films (the electron blocking film and the positive hole blocking film) is preferably 3 to 200 nm, more preferably 5 to 100 nm, and still more preferably 5 to 30 nm.

Substrate

The photoelectric conversion element may further include a substrate. The type of the substrate to be used is not particularly limited, and examples thereof include a semiconductor substrate, a glass substrate, and a plastic substrate.

The position of the substrate is not particularly limited, and in general, the conductive film, the photoelectric conversion film, and the transparent conductive film are laminated on the substrate in this order.

Sealing Layer

The photoelectric conversion element may further include a sealing layer. The performance of the photoelectric conversion material may deteriorate significantly due to the presence of deterioration factors such as water molecules. The deterioration can be prevented by sealing and coating the entire photoelectric conversion film with the sealing layer such as diamond-like carbon (DLC) or ceramics such as metal oxide, or metal nitride, and metal nitride oxide which are dense and into which water molecules do not permeate.

The material of the sealing layer may be selected and the sealing layer may be produced according to the description in paragraphs [0210] to [0215] of JP2011-082508A.

Optical Sensor

Examples of use of the photoelectric conversion element include the photoelectric cell and the optical sensor, but the photoelectric conversion element according to the embodiment of the present invention is preferably used as the optical sensor. The photoelectric conversion element may be used alone as the optical sensor. Alternately, the photoelectric conversion element may be used as a line sensor in which the photoelectric conversion elements are linearly arranged or as a two-dimensional sensor in which the photoelectric conversion elements are planarly arranged. In the line sensor, the photoelectric conversion element according to the embodiment of the present invention functions as the imaging element by converting optical image information into an electric signal using an optical system such as a scanner, and a driving unit. In the two-dimensional sensor, the photoelectric conversion element according to the embodiment of the present invention functions as the imaging element by converting the optical image information into the electric signal by imaging the optical image information on the sensor using the optical system such as an imaging module.

Imaging Element

Next, an example of a configuration of an imaging element comprising the photoelectric conversion element 10a will be described.

In the configuration example which will be described below, the same reference numerals or the corresponding reference numerals are attached to members or the like having the same configuration or action as those which have already been described, to simplify or omit the description.

The imaging element is an element that converts optical information of an image into the electric signal, and is an element in which a plurality of photoelectric conversion elements are arranged on a matrix in the same planar form, optical signals are converted into electric signals in each photoelectric conversion element (a pixel), and the electric signals can be sequentially output to the outside of the imaging elements for each pixel. For this reason, one pixel is composed of one photoelectric conversion element and one or more transistors.

Figure 3:
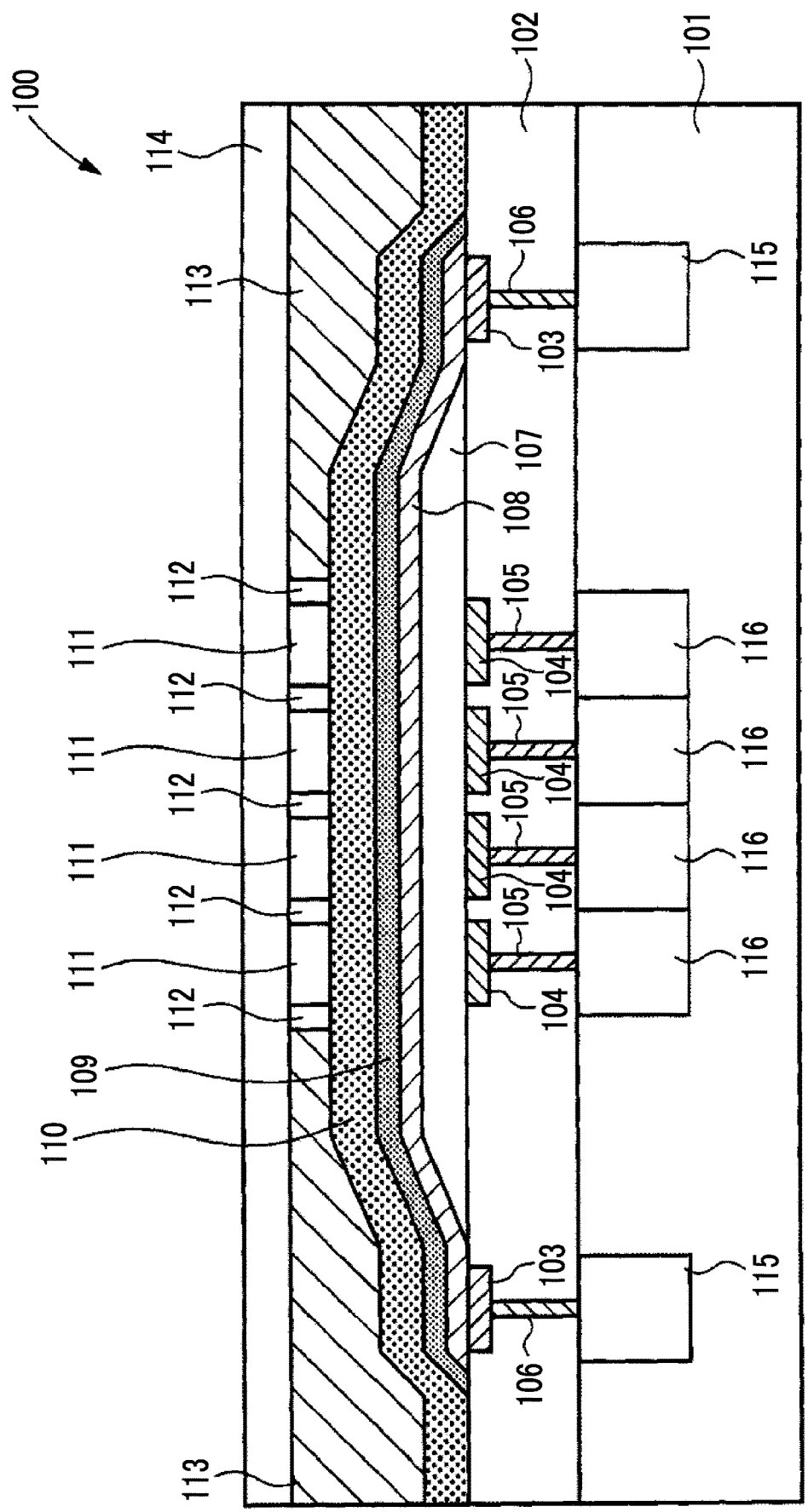
FIG. 3 is a schematic cross-sectional view of one pixel of an imaging element.

FIG. 3 is a schematic cross-sectional view showing a schematic configuration of an imaging element for describing an embodiment of the invention. This imaging element is mounted on an imaging device such as a digital camera and a digital video camera, an electronic endoscope, imaging modules such as a mobile phone, and the like.

The imaging element has a plurality of photoelectric conversion elements having configurations shown in FIG. 1A and a circuit substrate in which the readout circuit reading out signals corresponding to charges generated in the photoelectric conversion film of each photoelectric conversion element is formed. The imaging element has a configuration in which the plurality of photoelectric conversion elements are one-dimensionally or two-dimensionally arranged on the same surface above the circuit substrate.

An imaging element 100 shown in FIG. 3 comprises a substrate 101, an insulating layer 102, connection electrodes 103, pixel electrodes (lower electrodes) 104, connection units 105, connection units 106, a photoelectric conversion film 107, a counter electrode (upper electrode) 108, a buffer layer 109, a sealing layer 110, a color filter (CF) 111, partition walls 112, a light shielding layer 113, a protective layer 114, a counter electrode voltage supply unit 115, and readout circuits 116.

The pixel electrode 104 has the same function as the lower electrode 11 of the photoelectric conversion element 10a shown in FIG. 1A. The counter electrode 108 has the same function as the upper electrode 15 of the photoelectric conversion element 10a shown in FIG. 1A. The photoelectric conversion film 107 has the same configuration as a layer provided between the lower electrode 11 and the upper electrode 15 of the photoelectric conversion element 10a shown in FIG. 1A.

The substrate 101 is a semiconductor substrate such as the glass substrate or Si. The insulating layer 102 is formed on the substrate 101. A plurality of pixel electrodes 104 and a plurality of connection electrodes 103 are formed on the surface of the insulating layer 102.

The photoelectric conversion film 107 is a layer common to all the photoelectric conversion elements provided so as to cover the plurality of pixel electrodes 104.

The counter electrode 108 is one electrode common to all the photoelectric conversion elements provided on the photoelectric conversion film 107. The counter electrode 108 is formed on the connection electrodes 103 arranged on an outer side than the photoelectric conversion film 107, and is electrically connected to the connection electrodes 103.

The connection units 106 are buried in the insulating layer 102, and are plugs for electrically connecting the connection electrodes 103 to the counter electrode voltage supply unit 115. The counter electrode voltage supply unit 115 is formed in the substrate 101, and applies a predetermined voltage to the counter electrode 108 via the connection units 106 and the connection electrodes 103. In a case where a voltage to be applied to the counter electrode 108 is higher than a power supply voltage of the imaging element, the power supply voltage is boosted by a boosting circuit such as a charge pump to supply the predetermined voltage.

The readout circuits 116 are provided on the substrate 101 corresponding to each of the plurality of pixel electrodes 104, and read out signal according to charge trapped by the corresponding pixel electrodes 104. The readout circuits 116 are configured, for example, of CCD and CMOS circuits, or a thin film transistor (TFT) circuit, and are shielded by the light shielding layer not shown in the drawing which is disposed in the insulating layer 102. The readout circuits 116 are electrically connected to the corresponding the pixel electrodes 104 via the connection units 105.

The buffer layer 109 is formed on the counter electrode 108 so as to cover the counter electrode 108. The sealing layer 110 is formed on the buffer layer 109 so as to cover the buffer layer 109. The color filters 111 are formed on the sealing layer 110 at positions corresponding to each of the pixel electrodes 104. The partition walls 112 are provided between the color filters 111, and are used for improving the light transmittance of the color filters 111.

The light shielding layer 113 is formed on the sealing layer 110 in a region other than the region where the color filters 111 and the partition walls 112 are provided, and prevents light from being incident to the photoelectric conversion film 107 formed outside an effective pixel region. The protective layer 114 is formed on the color filters 111, the partition walls 112, and the light shielding layer 113, and protects the entirety of the imaging element 100.

In the imaging element 100 configured as described above, light which has entered is incident on the photoelectric conversion film 107, and charges are generated in the photoelectric conversion film. The positive holes among the generated charges are trapped by the pixel electrodes 104, and voltage signals corresponding to the amount are output to the outside of the imaging element 100 using the readout circuits 116.

A method of producing the imaging element 100 is as follows.

The connection units 105 and 106, the plurality of connection electrodes 103, the plurality of pixel electrodes 104, and the insulating layer 102 are formed on the circuit substrate in which the counter electrode voltage supply unit 115 and the readout circuits 116 are formed. The plurality of pixel electrodes 104 are disposed, for example, on the surface of the insulating layer 102 in a square grid shape.

Next, the photoelectric conversion film 107 is formed on the plurality of pixel electrodes 104, for example, by the vacuum evaporation method. Next, the counter electrode 108 is formed on the photoelectric conversion film 107 under vacuum, for example, by the sputtering method. Next, the buffer layer 109 and the sealing layer 110 are sequentially formed on the counter electrode 108, for example, by the vacuum evaporation method. Next, after the color filters 111, the partition walls 112, and the light shielding layer 113 are formed, the protective layer 114 is formed, and the production of the imaging element 100 is completed.

Compound

The present invention also includes the invention of compound. The compound according to an embodiment of the present invention is the same as the compound represented

EXAMPLES

Examples will be shown below, but the invention is not limited thereto.

Compound Used for Photoelectric Conversion Film

<Synthesis of Compound (D-4)>

A compound (D-4) was synthesized according to the following scheme.

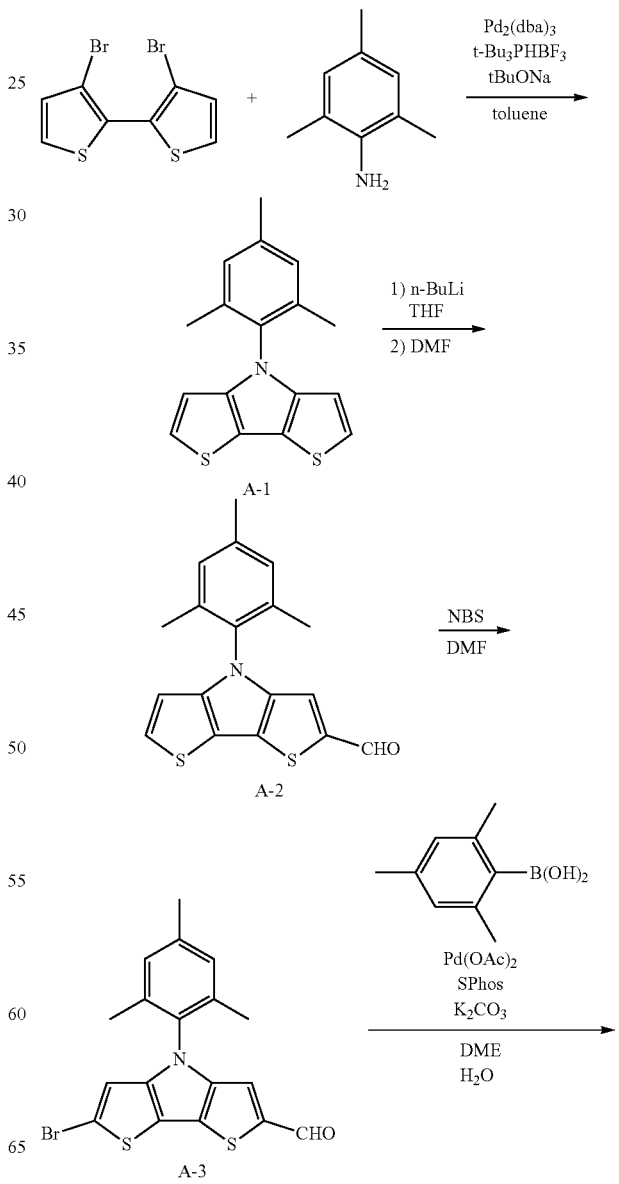

-continued

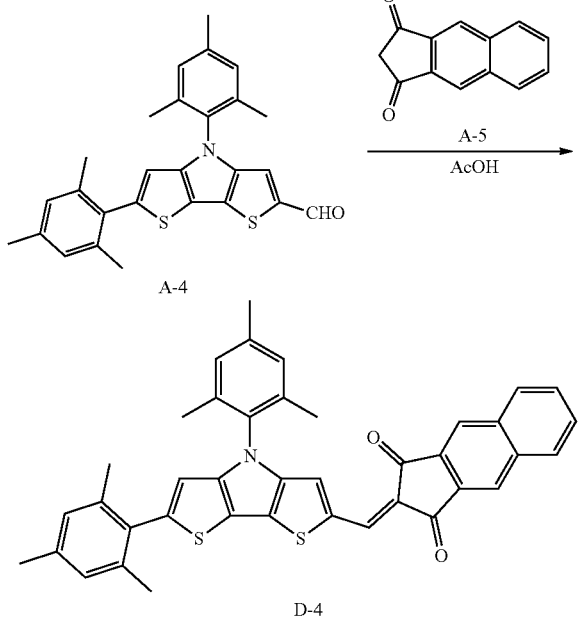

2,4,6-trimethylaniline (22.5 g, 167 mmol), 3,3-dibromo-2,2-bithiophene (36.0 g, 111 mmol), and t-butoxy sodium (32.0 g, 333 mmol) were added to toluene, and the solution was degassed by performing pressure reduction and nitrogen replacement. Tris(dibenzylideneacetone) dipalladium(0) (Pd$_2$(dba)$_3$) (10.2 g, 11.1 mmol) and tri-t-butylphosphonium tetrafluoroborate (t-Bu$_3$PHBF$_4$) (3.22 g, 11.1 mmol) were added to the obtained solution, and the solution was further heated to reflux to perform a reaction. After allowing the solution to react for 2.5 hours, the solution was allowed to cool to room temperature, and saturated saline (300 mL) was added thereto. Ethyl acetate was added to the solution for liquid separation, and an organic phase was separated. Magnesium sulfate was added to the organic phase, the organic phase was filtered, and the obtained filtrate was concentrated to obtain a crude product. The obtained crude product was purified by silica gel column chromatography (eluent: hexane) to obtain a compound (A-1) (9.30 g, yield 28%).

The compound (A-1) (6.00 g, 20.2 mmol) was dissolved in tetrahydrofuran (THF) (100 mL) and cooled to −78° C., and a 1.6 M hexane solution of n-butyllithium (n-BuLi) (13.9 mL, 22.2 mmol) was added dropwise thereto over 7 minutes. After allowing the obtained solution to react at −78° C. for 40 minutes, N,N-dimethylformamide (DMF) (3.13 mL, 40.4 mmol) was added dropwise thereto over 5 minutes. Thereafter, the solution was heated to an internal temperature of 5 C, allowed to react for 40 minutes, and then water (70 mL) was added thereto. Ethyl acetate was added to the solution for liquid separation, and an organic phase was separated. Magnesium sulfate was added to the organic phase, the organic phase was filtered, and the obtained filtrate was concentrated to obtain a crude product. The obtained crude product was purified by silica gel column chromatography (eluent: 15% ethyl acetate/hexane) to obtain a compound (A-2) (5.70 g, yield 87%).

The compound (A-2) was added to N,N-dimethylformamide (DMF) (57 mL) and stirred, and N-bromosuccinimide (NBS) (3.27 g, 18.4 mmol) was added thereto. After allowing the obtained solution to react at room temperature (23±3° C.) for 1 hour, water (100 mL) and ethyl acetate (100 mL) were added to the solution for liquid separation, and an organic phase was separated. After washing the organic phase with saturated saline, magnesium sulfate was added thereto, the organic phase was filtered, and the obtained filtrate was concentrated to obtain a crude product. The obtained crude product was purified by silica gel column chromatography (eluent: 20% ethyl acetate/hexane) to obtain a compound (A-3) (5.31 g, yield 75%).

The compound (A-3) (1.21 g, 3.0 mmol), 2,4,6-trimethylphenylboronic acid (0.98 g, 6.0 mmol), and potassium carbonate (1.24 g, 9.0 mmol) were added to a mixed solvent of 1,2-dimethoxyethane (DME) (30 mL) and water (3.0 mL). The obtained solution was degassed by performing pressure reduction and nitrogen replacement. Palladium(II) acetate (67 mg, 0.30 mmol) and dicyclohexylphosphino-2,2-dimethoxyphenyl (246 mg, 0.60 mmol) were added to the solution, and the solution was heated to reflux to perform a reaction. After allowing the solution to react for 8 hours, the solution was allowed to cool to room temperature, and saturated saline (300 mL) was added thereto. Ethyl acetate was added to the solution for liquid separation, and an organic phase was separated. Magnesium sulfate was added to the organic phase, the organic phase was filtered, and the obtained filtrate was concentrated to obtain a crude product. The obtained crude product was purified by silica gel column chromatography (eluent: 15% ethyl acetate/hexane) to obtain a compound (A-4) (8.70 mg, yield 65%).

The compound (A-4) (350 mg, 0.79 mmol) and the compound (A-5) (163 mg, 0.83 mmol) was added to acetic acid (AcOH) (3.5 mL). The obtained solution was allowed to react at 100° C. for 3 hours. After allowing the solution to cool, the solution was filtered, and the obtained filtered product was washed with methanol to obtain a crude product. The obtained crude product was recrystallized from toluene to obtain a compound (D-4) (398 mg, yield 81%).

The obtained compound (D-4) was identified by $^1$H nuclear magnetic resonance (NMR) and mass spectrometry (MS).

Figure 4:
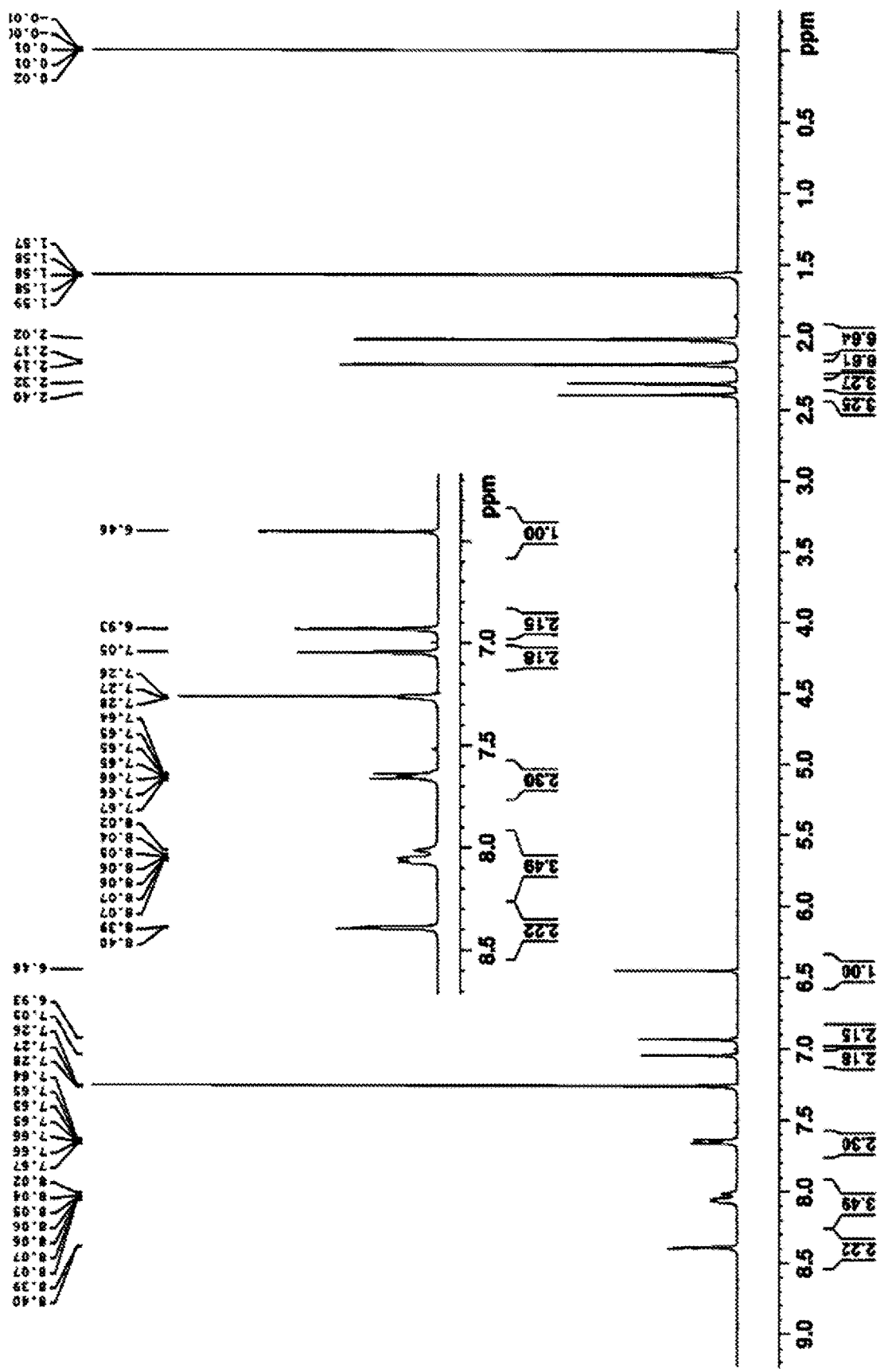
FIG. 4 is a $^1$H nuclear magnetic resonance (NMR) chart of a compound (D-4).

FIG. 4 shows a $^1$H NMR spectrum (400 MHz, CDCl$_3$).

MS (ESI$^+$) m/z: 621.3 ([M+H]$^+$)

<Synthesis of Compound (D-13)>

A compound (D-13) was synthesized according to the following scheme.

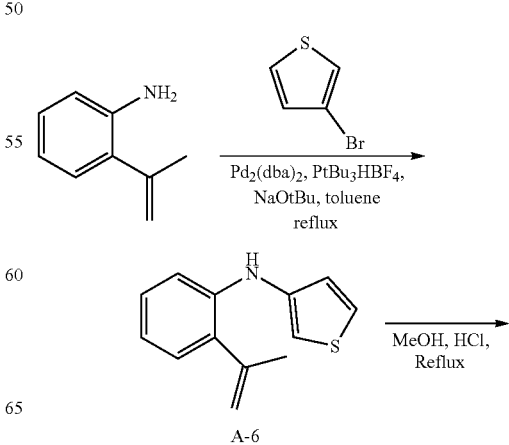

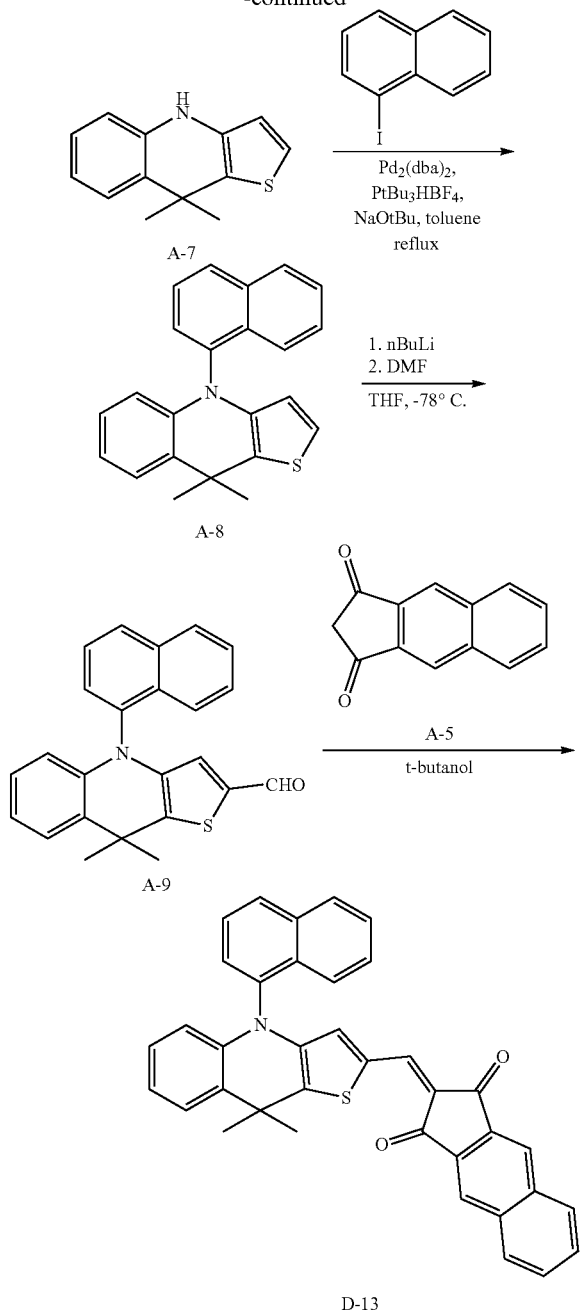

2-isopropenylaniline (40.0 g, 300 mmol), 3-bromothiophene (49.5 g, 304 mmol), tris(dibenzylideneacetone) dipalladium(0) (Pd$_2$(dba)$_3$) (2.75 g, 3.00 mmol), tri-tert-butylphosphonium tetrafluoroborate (P(tBu$_3$)HBF$_4$) (1.78 g, 6.00 mmol), sodium tert-butoxide (NaOtBu) (40.4 g, 420 mmol), and toluene (800 mL) were charged into a 2 L 3-neck flask, and the solution was degassed and replaced with nitrogen gas. Under a nitrogen atmosphere, the obtained solution was heated to 110° C. and stirred for 5 hours. Thereafter, the solution was cooled to room temperature, water was added to the solution, and the solution was separated into a water phase and an organic phase. The organic phase was extracted and washed with ethyl acetate and brine, and concentrated under reduced pressure. The concentrated residue was purified by silica gel column chromatography (eluent: "toluene:hexane=1:3") to obtain a compound (A-6) (45.0 g, yield 70%) as a pale yellow viscous liquid.

The compound (A-6) (45.0 g, 209 mmol) was dissolved in methanol (1000 mL), a 30% hydrochloric acid (80 mL) was added thereto, and the solution was allowed to react for 2 hours while heating to reflux. After cooling the reacted solution to room temperature, 900 mL of methanol was distilled from the solution, an organic phase in the solution was extracted and washed with ethyl acetate and brine, and then the organic phase was concentrated under reduced pressure. The concentrated residue was purified by silica gel column chromatography (eluent: "toluene:hexane=1:3") to obtain a compound (A-7) (6.4 g, yield 14%) as a pale yellow solid.

The compound (A-7) (2.20 g, 10.2 mmol), 1-iodonaphthalene (3.89 g, 15.3 mmol), tris(dibenzylideneacetone) dipalladium(0) (Pd$_2$(dba)$_3$) (187 mg, 0.204 mmol), tri-tert-butylphosphonium tetrafluoroborate (P(tBu$_3$)HBF$_4$) (121 mg, 0.408 mmol), sodium tert-butoxide (NaOtBu) (1.47 g, 15.3 mmol), and toluene (10 mL) were charged into a 50 mL 3-neck flask, and the solution was degassed and replaced with nitrogen gas. Under a nitrogen atmosphere, the obtained solution was heated to 110° C. and stirred for 4 hours. Thereafter, the solution was cooled to room temperature, water was added to the solution, and the solution was separated into a water phase and an organic phase. The organic phase was extracted and washed with ethyl acetate and brine, and concentrated under reduced pressure. The concentrated residue was purified by silica gel column chromatography (eluent: "toluene:hexane=1:5") to obtain a compound (A-8) (2.90 g, yield 83%) as a pale yellow solid.

The compound (A-8) (1.70 g, 4.98 mmol) was dissolved in tetrahydrofuran (THF) (17 mL) and cooled to −78° C. under a nitrogen atmosphere. A 1.6 M hexane solution of n-butyllithium (n-BuLi) (6.23 mL, 9.96 mmol) was added dropwise thereto, and the solution was stirred for 10 minutes. N,N-dimethylformamide (DMF) (728 mL, 9.96 mmol) was added dropwise to the solution, and the solution was stirred for 30 minutes. After returning the solution to room temperature, diluted hydrochloric acid was added. An organic phase in the solution was extracted and washed with ethyl acetate and brine, and concentrated under reduced pressure. The concentrated residue was purified by silica gel column chromatography (eluent: toluene) to obtain a compound (A-9) (1.61 g, yield 88%) as a yellow solid.

The compound (A-9) (1.61 g, 4.36 mmol) and the compound (A-5) (940 mg, 4.80 mmol) were added to 1-butanol (60 mL), and the solution was allowed to react for 2 hours at 110° C. After cooling the solution to room temperature, the precipitated solid was filtered and the filtered product was washed with acetonitrile to obtain a crude product. The obtained crude product was purified by silica gel column chromatography (eluent: "chloroform:ethyl acetate=9:1") and further recrystallized from a mixed solvent of chloroform-acetonitrile, and the obtained solid was washed with acetonitrile to obtain a compound (D-13) (850 mg, yield 36%).

The obtained compound (D-13) was identified by $^1$H nuclear magnetic resonance (NMR) and mass spectrometry (MS).

Figure 5:
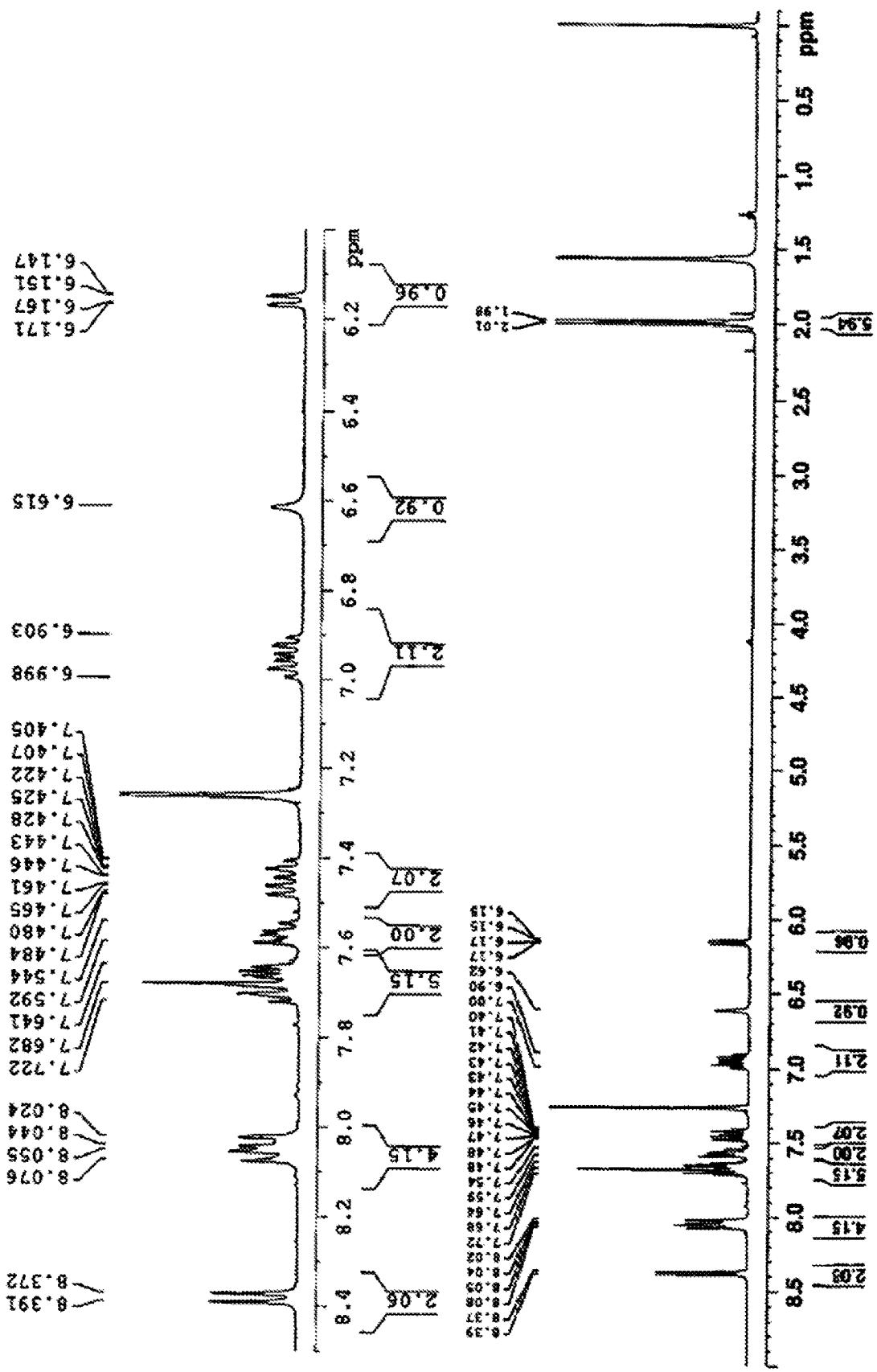
FIG. 5 is a $^1$H nuclear magnetic resonance (NMR) chart of a compound (D-13).

FIG. 5 shows a $^1$H NMR spectrum (400 MHz, CDCl$_3$). MS (ESI$^+$) m/z: 548.2 ([M+H]$^+$)

With reference to the above-described synthesis method of the compound (D-4), compounds (D-1) to (D-3), and (D-5) to (D-11) were further synthesized.

With reference to the above-described synthesis method of the compound (D-13), compounds (D-12), (D-14), and (D-15) were further synthesized.

The structures of the obtained compounds (D-1) to (D-15) and the comparative compounds (R-1) and (R-2) are shown below. In a case where the compounds were applied to Formula (1) or (2), the structural formula for the obtained compounds (D-1) to (D-15) shown below means to include both the cis isomer and the trans isomer which are distinguished based on a group corresponding to the C=C double bond composed of a carbon atom to which $R^2$ is bonded and a carbon atom adjacent thereto.

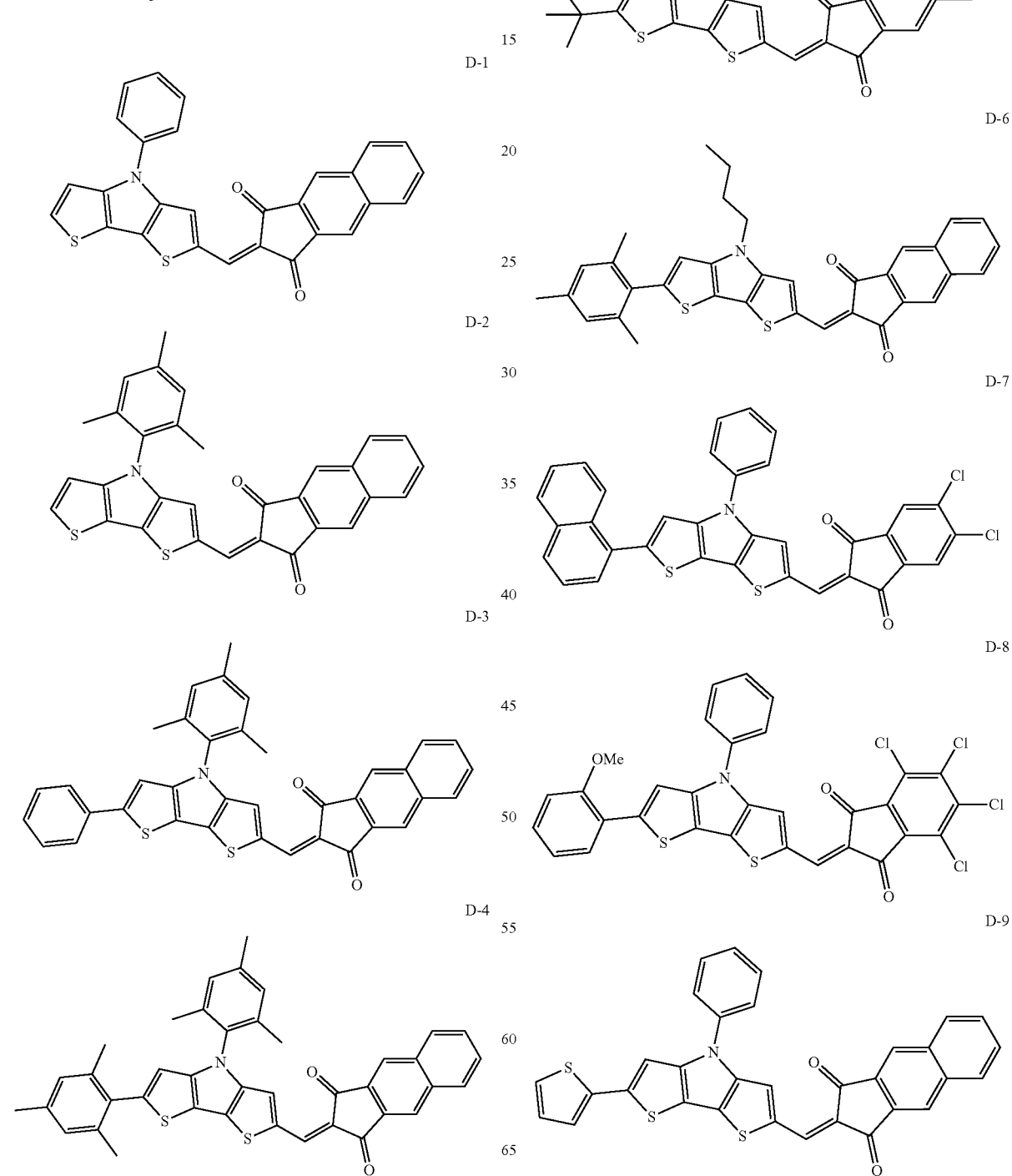

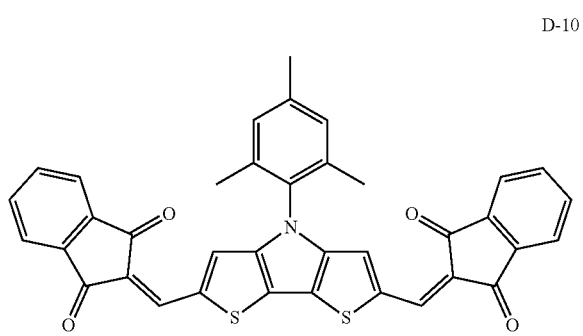

D-10

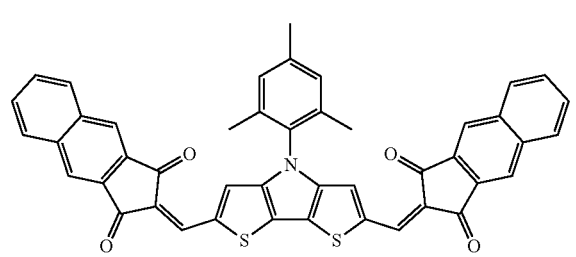

D-11

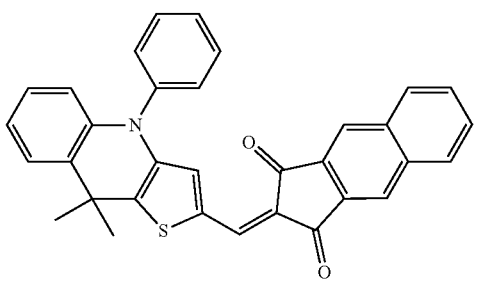

D-12

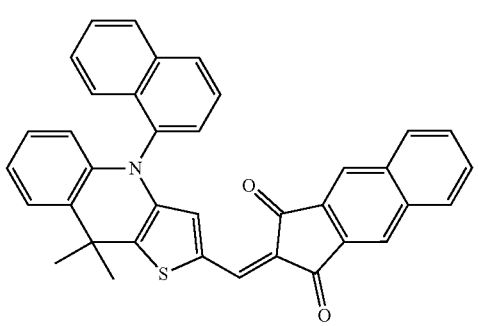

D-13

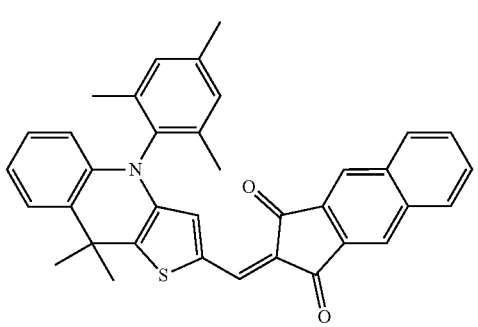

D-14

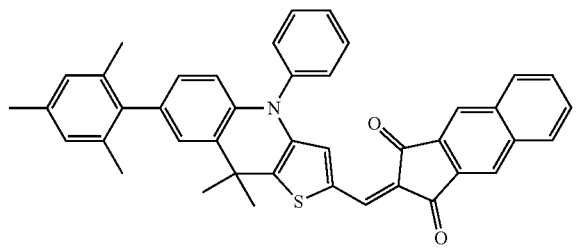

D-15

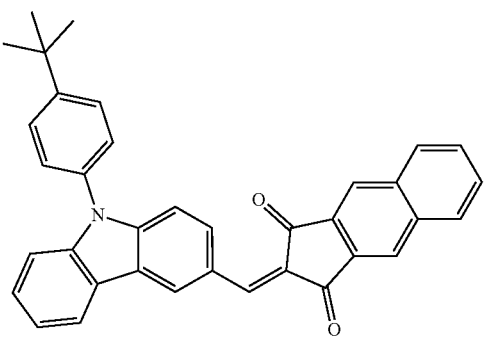

R-1

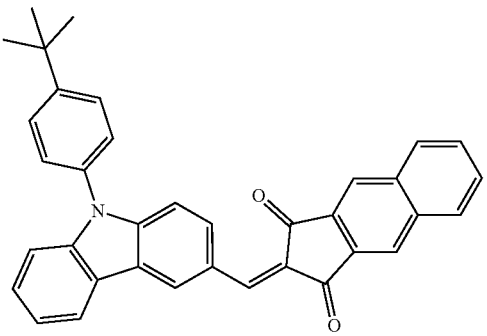

R-2

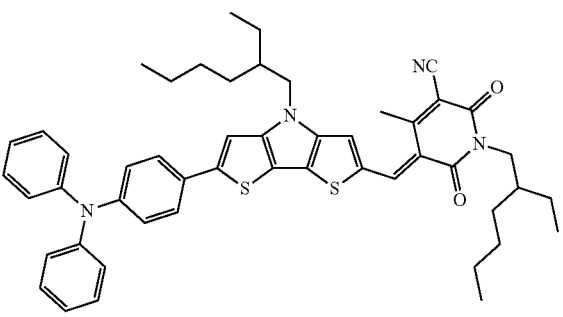

Evaluation

<Production of Photoelectric Conversion Element (Element (A))>

The photoelectric conversion element of the form of FIG. 1A was produced using the obtained compound. In other words, the photoelectric conversion element to be evaluated in the present example is formed of the lower electrode 11, the electron blocking film 16A, the photoelectric conversion film 12, and the upper electrode 15.

Specifically, an amorphous ITO was formed into a film on the glass substrate by the sputtering method to form the lower electrode 11 (a thickness: 30 nm). Furthermore, the compound (EB-1) was formed into a film on the lower electrode 11 by the vacuum evaporation method to form the electron blocking film 16A (a thickness: 10 nm).

Furthermore, the compound (D-1) as the p-type organic semiconductor and the fullerene ($C_{60}$) as the n-type organic semiconductor were subjected to co-vapor deposition by the vacuum evaporation method so as to be respectively 100 nm in terms of single layer on the electron blocking film 16A to form a film in a state in which the temperature of the substrate was controlled to 25° C., and the photoelectric conversion film 12 having the bulk hetero structure of 200 nm was formed.

Furthermore, amorphous ITO was formed into a film on the photoelectric conversion film 12 by a sputtering method to form the upper electrode 15 (the transparent conductive film) (the thickness: 10 nm). After the SiO film was formed as the sealing layer on the upper electrode 15 by a vacuum evaporation method, an aluminum oxide ($Al_2O_3$) layer was formed thereon by an atomic layer chemical vapor deposition (ALCVD) method to produce a photoelectric conversion element.

The obtained photoelectric conversion element was to be an element ($A_{D-1}$).

Same as described above, elements ($A_{D-2}$) to ($A_{D-15}$) and ($A_{R-1}$) were produced using the compounds (D-2) to (D-15) and (R-1) (these photoelectric conversion elements are collectively referred to as the element (A)).

In addition, in a case where the production of photoelectric conversion element was attempted using the compound (R-2), the compound (R-2) could not be vapor-deposited on the electron blocking film 16A, and thus the photoelectric conversion element could not be produced.

EB-1

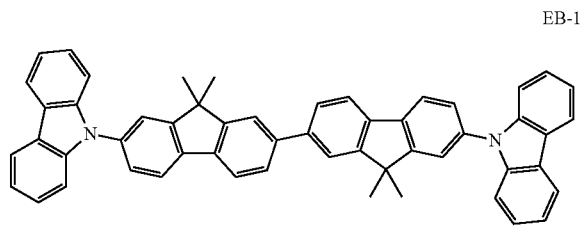 [SMILES: CC1(C)c2cc(-c3ccc4c(c3)C(C)(C)c3cc(-n5c6ccccc6c6ccccc65)ccc3-4)ccc2-c2ccc(-n3c4ccccc4c4ccccc43)cc21]

<Confirmation of Driving (Evaluation of Photoelectric Conversion Efficiency (External Quantum Efficiency))>

The driving of each of the obtained photoelectric conversion elements was confirmed. A voltage was applied to each of the photoelectric conversion elements so that the electric field strength was $1.0 \times 10^5$ V/cm. Thereafter, in a case of measuring photoelectric conversion efficiency (external quantum efficiency) at 540 nm by irradiating with light from the upper electrode (transparent conductive film) side, it was confirmed that all the elements (A) produced using the compounds (D-1) to (D-15) and (R-1) exhibit 60% or more photoelectric conversion efficiency and have a sufficient external quantum efficiency as the photoelectric conversion element. The external quantum efficiency was measured using a constant energy quantum efficiency measuring device manufactured by Optel. The amount of light irradiated was 50 μW/cm$^2$.

<Evaluation of Heat Resistance of Photoelectric Conversion Element>

After heating each of the obtained elements (A) on a hot plate at 160° C. for 1 hour, a voltage was applied so that the photoelectric conversion efficiency at the maximum absorption wavelength was 60%, and the dark current at the voltage was measured. In a case where the dark current in the same measurement before heating was 1, heat resistance of the photoelectric conversion element was evaluated by a relative value of the dark current after heating.

It is preferable that the measured value of the dark current was small.

A case where the relative value was less than 1.5 was A, a case where the relative value was 1.5 or more and less than 2.0 was B, and a case where the relative value was 2.0 or more was C. The results are shown in Table 1. Practically, B or more is preferable and A is more preferable.

TABLE 1

| | Compound | Element | Film heat resistance |
|---|---|---|---|
| Example 1 | D-1 | $A_{D-1}$ | A |
| Example 2 | D-2 | $A_{D-2}$ | A |
| Example 3 | D-3 | $A_{D-3}$ | A |
| Example 4 | D-4 | $A_{D-4}$ | A |
| Example 5 | D-5 | $A_{D-5}$ | A |
| Example 6 | D-6 | $A_{D-6}$ | B |
| Example 7 | D-7 | $A_{D-7}$ | A |
| Example 8 | D-8 | $A_{D-8}$ | A |
| Example 9 | D-9 | $A_{D-9}$ | A |
| Example 10 | D-10 | $A_{D-10}$ | A |
| Example 11 | D-11 | $A_{D-11}$ | A |
| Example 12 | D-12 | $A_{D-12}$ | A |
| Example 13 | D-13 | $A_{D-13}$ | A |
| Example 14 | D-14 | $A_{D-14}$ | A |
| Example 15 | D-15 | $A_{D-15}$ | A |
| Comparative Example 1 | R-1 | $A_{R-1}$ | C |
| Comparative Example 2 | R-2 | | Not forming film |

From the results shown in the table, it was confirmed that the photoelectric conversion element according to the embodiment of the present invention has excellent heat resistance.

In addition, in the specific compound, it was confirmed that, in a case where a group corresponding to $R^1$ in Formulae (1) and (2) is an aryl group which may have a substituent, the photoelectric conversion element has more excellent heat resistance.

<Production of Imaging Element>

In a case where the same imaging element as shown in FIG. 3 was produced using the elements (AD-1) to (AD-15) after performing the <Evaluation of Heat Resistance of Photoelectric Conversion Element>, the imaging element did not have a problem in performance

EXPLANATION OF REFERENCES 10a, 10b: photoelectric conversion element
11: conductive film (lower electrode)
12: photoelectric conversion film
15: transparent conductive film (upper electrode)
16A: electron blocking film
16B: positive hole blocking film
100: pixel separation type imaging element
101: substrate
102: insulating layer
103: connection electrode
104: pixel electrode (lower electrode)
105: connection unit
106: connection unit
107: photoelectric conversion film
108: counter electrode (upper electrode)
109: buffer layer
110: sealing layer
111: color filter (CF)
112: partition wall
113: light shielding layer
114: protective layer
115: counter electrode voltage supply unit
116: readout circuit
200: photoelectric conversion element (hybrid type photoelectric conversion element)
201: inorganic photoelectric conversion film
202: n-type well
203: p-type well
204: n-type well 205: p-type silicon substrate
207: insulating layer
208: pixel electrode
209: organic photoelectric conversion film
210: common electrode
211: protective film
212: electron blocking film

What is claimed is:

1. A photoelectric conversion element comprising:
a conductive film;
a photoelectric conversion film; and
a transparent conductive film in this order,
wherein the photoelectric conversion film includes at least one compound selected from the group consisting of a compound represented by Formula (1) and a compound represented by Formula (2),

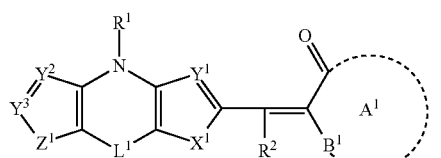
(1)

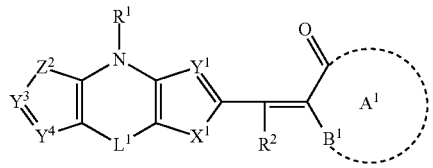
(2)

in Formulae (1) and (2), $R^1$ represents a hydrogen atom, an aryl group which may have a substituent, or a heteroaryl group which may have a substituent, $R^2$ represents a hydrogen atom or a substituent, $X^1$ represents a sulfur atom, an oxygen atom, a selenium atom, a tellurium atom, $-NR^{a1}-$, $-CR^{a2}R^{a3}-$, or $-SiR^{a4}R^{a5}-$, $Y^1$ to $Y^4$ each independently represent $-CR^{a6}=$ or a nitrogen atom, $L^1$ represents a single bond, an oxygen atom, a sulfur atom, a selenium atom, a tellurium atom, $-NR^{a7}-$, $-CR^{a8}R^{a9}-$, $-SiR^{a10}R^{a11}-$, or $-CO-$, in a case where $L^1$ is a single bond, $Z^1$ and $Z^2$ each independently represent a sulfur atom, an oxygen atom, a selenium atom, a tellurium atom, $-NR^{a12}-$, $-CR^{a13}R^{a14}-$, $-SiR^{a15}R^{a16}-$, or $-CO-$, in a case where $L^1$ is an oxygen atom, a sulfur atom, a selenium atom, a tellurium atom, $-NR^{a7}-$, $-CR^{a8}R^{a9}-$, $-SiR^{a10}R^{a11}-$, or $-CO-$, $Z^1$ and $Z^2$ each independently represent a sulfur atom, an oxygen atom, a selenium atom, a tellurium atom, $-NR^{a12}-$, $-CR^{a13}R^{a14}-$, $-SiR^{a15}R^{a16}-$, $-CO-$, or $-CR^{a17}=CR^{a18}-$, $B^1$ represents $-CO-$, an oxygen atom, a sulfur atom, a selenium atom, a tellurium atom, $-NR^{a19}-$, $-CR^{a20}R^{a21}-$, or $-SiR^{a22}R^{a23}-$, $R^{a1}$ to $R^{a23}$ each independently represent a hydrogen atom or a substituent, $A^1$ represents a ring, in Formula (1), $R^1$, $R^2$, and $R^{a1}$ to $R^{a23}$ may be respectively bonded to each other to form a ring, and in Formula (2), $R^1$, $R^2$, and $R^{a1}$ to $R^{a23}$ may be respectively bonded to each other to form a ring.

2. The photoelectric conversion element according to claim 1,
wherein the compound represented by Formula (1) is a compound represented by Formula (3), and
the compound represented by Formula (2) is a compound represented by Formula (4),

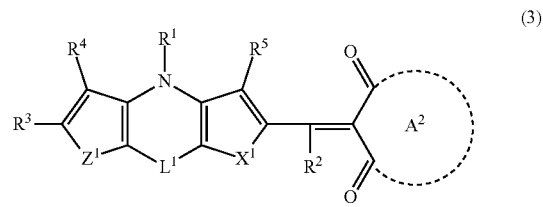
(3)

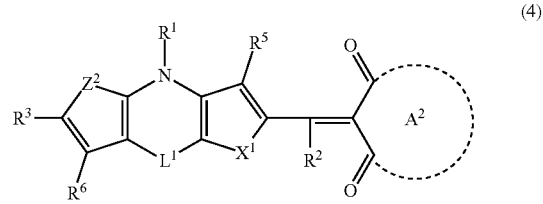
(4)

in Formulae (3) and (4), $R^1$ represents a hydrogen atom, an aryl group which may have a substituent, or a heteroaryl group which may have a substituent, $R^2$ to $R^6$ each independently represent a hydrogen atom or a substituent, $X^1$ represents a sulfur atom, an oxygen atom, a selenium atom, a tellurium atom, $-NR^{a1}-$, $-CR^{a2}R^{a3}-$, or $-SiR^{a4}R^{a5}-$, $L^1$ represents a single bond, an oxygen atom, a sulfur atom, a selenium atom, a tellurium atom, $-NR^{a7}-$, $-CR^{a8}R^{a9}-$, $-SiR^{a10}R^{a11}-$, or $-CO-$, in a case where $L^1$ is a single bond, $Z^1$ and $Z^2$ each independently represent a sulfur atom, an oxygen atom, a selenium atom, a tellurium atom, $-NR^{a12}-$, $-CR^{a13}R^{a14}-$, $-SiR^{a15}R^{a16}-$, or $-CO-$, in a case where $L^1$ is an oxygen atom, a sulfur atom, a selenium atom, a tellurium atom, $-NR^{a7}-$, $-CR^{a8}R^{a9}-$, $-SiR^{a10}R^{a11}-$, or $-CO-$, $Z^1$ and $Z^2$ each independently represent a sulfur atom, an oxygen atom, a selenium atom, a tellurium atom, $-NR^{a12}-$, $-CR^{a13}R^{a14}-$, $-SiR^{a5}R^{a16}-$, $-CO-$, or $-CR^{a17}=CR^{a18}-$, $R^{a1}$ to $R^{a5}$ and $R^{a7}$ to $R^{a18}$ each independently represent a hydrogen atom or a substituent, $A^2$ represents a ring, in Formula (3), $R^1$ to $R^5$, $R^{a1}$ to $R^{a5}$, and $R^{a7}$ to $R^{a1}$s may be respectively bonded to each other to form a ring, and in Formula (4), $R^1$ to $R^3$, $R^5$, $R^6$, $R^{a1}$ to $R^{a5}$, and $R^{a7}$ to $R^{a18}$ may be respectively bonded to each other to form a ring.

3. The photoelectric conversion element according to claim 1,
wherein $L^1$ represents a single bond or $-CR^{a8}R^{a9}-$.

4. The photoelectric conversion element according to claim 1,
wherein $X^1$ represents a sulfur atom, an oxygen atom, or a selenium atom.

5. The photoelectric conversion element according to claim 1,
wherein the photoelectric conversion film includes a compound represented by Formula (5),

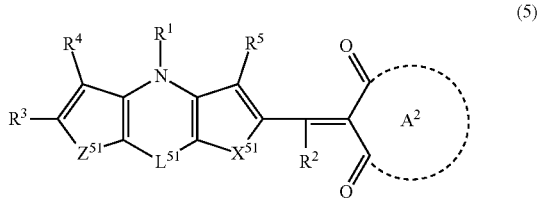

in Formula (5), $R^1$ represents a hydrogen atom, an aryl group which may have a substituent, or a heteroaryl group which may have a substituent, $R^2$ to $R^5$ each independently represent a hydrogen atom or a substituent, $X^{51}$ represents a sulfur atom or an oxygen atom, $L^{51}$ represents a single bond or —$CR^{a51}R^{a52}$—, in a case where $L^{51}$ is a single bond, $Z^{51}$ represents a sulfur atom or an oxygen atom, in a case where $L^{51}$ is —$CR^{a51}R^{a52}$—, $Z^{51}$ represents a sulfur atom, an oxygen atom, or —$CR^{a53}$=$CR^{a54}$—, $R^{a15}$ to $R^{a54}$ each independently a hydrogen atom or a substituent, $A^2$ represents a ring, and $R^1$ to $R^5$, and $R^{a51}$ to $R^{a54}$ may be respectively bonded to each other to form a ring.

6. The photoelectric conversion element according to claim 5,
wherein the compound represented by Formula (5) is a compound represented by Formula (6),

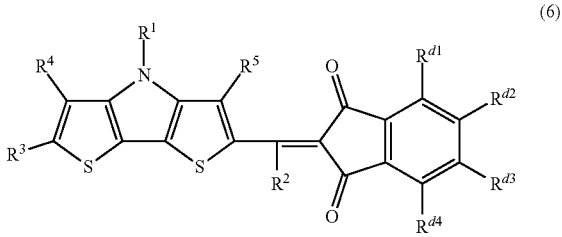

in Formula (6), $R^1$ represents a hydrogen atom, an aryl group which may have a substituent, or a heteroaryl group which may have a substituent, $R^2$ to $R^5$, and $R^{d1}$ to $R^{d4}$ each independently represent a hydrogen atom or a substituent, and $R^1$ to $R^5$, and $R^{d1}$ to $R^{d4}$ may be respectively bonded to each other to form a ring.

7. The photoelectric conversion element according to claim 1,
wherein molecular weights of the compound represented by Formula (1) and the compound represented by Formula (2) are 400 to 900 amu.

8. The photoelectric conversion element according to claim 1,
wherein the photoelectric conversion film further includes an n-type organic semiconductor, and
the photoelectric conversion film has a bulk hetero structure formed in a state which the n-type organic semiconductor is mixed with the at least one compound selected from the group consisting of the compound represented by Formula (1) and the compound represented by Formula (2).

9. The photoelectric conversion element according to claim 1, further comprising:
one or more interlayers between the conductive film and the transparent conductive film, in addition to the photoelectric conversion film.

10. An optical sensor comprising:
the photoelectric conversion element according to claim 1.

11. An imaging element comprising:
the photoelectric conversion element according to claim 1.

12. A compound represented by Formula (5),

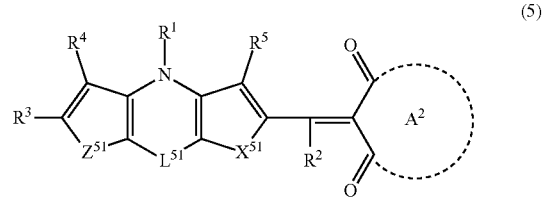

in Formula (5), $R^1$ represents a hydrogen atom, an aryl group which may have a substituent, or a heteroaryl group which may have a substituent, $R^2$ to $R^5$ each independently represent a hydrogen atom or a substituent, $X^{51}$ represents a sulfur atom or an oxygen atom, $L^{51}$ represents a single bond or —$CR^{a5}R^{a52}$—, in a case where $L^{51}$ is a single bond, $Z^{51}$ represents a sulfur atom or an oxygen atom, in a case where $L^{51}$ is —$CR^{a51}R^{a52}$—, $Z^{51}$ represents a sulfur atom, an oxygen atom, or —$CR^{a53}$=$CR^{a54}$—, $R^{a51}$ to $R^{a54}$ each independently a hydrogen atom or a substituent, $A^2$ represents a ring, and $R^1$ to $R^5$, and $R^{a51}$ to $R^{a54}$ may be respectively bonded to each other to form a ring.

13. The photoelectric conversion element according to claim 2,
wherein $L^1$ represents a single bond or —$CR^{a8}R^{a9}$—.

14. The photoelectric conversion element according to claim 2,
wherein $X^1$ represents a sulfur atom, an oxygen atom, or a selenium atom.

15. The photoelectric conversion element according to claim 2,
wherein molecular weights of the compound represented by Formula (1) and the compound represented by Formula (2) are 400 to 900 amu.

16. The photoelectric conversion element according to claim 2,
wherein the photoelectric conversion film further includes an n-type organic semiconductor, and
the photoelectric conversion film has a bulk hetero structure formed in a state which the n-type organic semiconductor is mixed with the at least one compound selected from the group consisting of the compound represented by Formula (1) and the compound represented by Formula (2).

17. The photoelectric conversion element according to claim 2, further comprising:
one or more interlayers between the conductive film and the transparent conductive film, in addition to the photoelectric conversion film.

18. An optical sensor comprising:
the photoelectric conversion element according to claim 2.

19. An imaging element comprising:
the photoelectric conversion element according to claim 2.

20. The photoelectric conversion element according to claim 3,
wherein $X^1$ represents a sulfur atom, an oxygen atom, or a selenium atom.

* * * * *